US 6,620,767 B1

(12) United States Patent
Ducray et al.

(10) Patent No.: US 6,620,767 B1
(45) Date of Patent: Sep. 16, 2003

(54) PESTICIDAL N-HETEROARYL ALPHA-ALKOXIMINO-CARBOXAMIDES

(75) Inventors: Pierre Ducray, Saint-Louis (FR); Jacques Bouvier, Neuchatel (CH)

(73) Assignee: Novartis Animal Health US, Inc., Greensboro, NC (US)

( * ) Notice: Subject to any disclaimer, the term of this patent is extended or adjusted under 35 U.S.C. 154(b) by 0 days.

(21) Appl. No.: 10/148,163

(22) PCT Filed: Nov. 27, 2000

(86) PCT No.: PCT/EP00/11840

§ 371 (c)(1),
(2), (4) Date: May 28, 2002

(87) PCT Pub. No.: WO01/40206

PCT Pub. Date: Jun. 7, 2001

(30) Foreign Application Priority Data

Nov. 29, 1999 (CH) ............................................... 2175/99

(51) Int. Cl.$^7$ ............................................... A01N 43/82
(52) U.S. Cl. ...................... 504/262; 514/361; 548/128; 548/197; 548/214; 549/68
(58) Field of Search ................................. 548/128, 197, 548/214; 504/262; 514/361; 549/68

(56) References Cited

U.S. PATENT DOCUMENTS 5,942,528 A * 8/1999 Heil et al. .................. 514/361

* cited by examiner

Primary Examiner—Joseph K. McKane
Assistant Examiner—Robert Shiao
(74) Attorney, Agent, or Firm—Michael U. Lee

(57) ABSTRACT

The invention relates to compounds of the general formula $$
\text{R}_1 \text{—} \underset{\underset{\text{S}}{X_2}}{\overset{X_1}{\diagdown}} \text{—} \underset{X_3}{\overset{R_2}{N}} \text{—} \overset{N-OR_3}{\underset{}{C}} \text{—} (Q)_n \text{—} X_4 \text{—} R_4,
$$
I wherein $R_1$ is hydrogen, halogen, $C_1$–$C_6$-alkyl, $C_1$–$C_6$-alkoxy, $C_1$–$C_6$-haloalkyl or unsubstituted or mono- to penta-substituted phenyl, whereby the substituents are selected from the group comprising $C_1$–$C_6$-alkyl, $C_1$–$C_6$-haloalkyl, $C_1$–$C_6$-alkoxy, aryloxy, halogen, cyano and nitro, whereby if the number of substituents is greater than 1, the substituents may be identical or different; $R_2$ is hydrogen, $C_1$–$C_6$-alkyl, ($C_1$–$C_6$-alkylene)phenyl, pyridyl, $COOR_6$, $CONR_7R_8COR_6$, allyl or $CH_2$—O—$R_6$; $R_3$ is $C_1$–$C_6$-alkyl; $R_4$ is unsubstituted or substituted phenyl, unsubstituted or substituted benzyl or unsubstituted or substituted heterocyclyl, whereby each of the substituents, independently of each other, is selected from the group comprising $C_1$–$C_6$-alkyl, $C_1$–$C_6$-haloalkyl, $C_1$–$C_6$-alkoxy, aryloxy, halogen, cyano, hydroxy, amino and nitro, whereby if the number of substituents is greater than 1, the substituents may be identical or different; $R_6$ is $C_1$–$C_6$-alkyl, phenyl or benzyl; $R_7$ and $R_8$ independently of one another, are hydrogen or $C_1$–$C_6$-alkyl; Q is $C_1$–$C_6$-alkylene; $X_1$ is N or C(CN); $X_2$ is N, C(CN), C($COOR_6$), C($COR_6$), C($SOR_6$), C($CONR_7R_8$) or C($NO_2$); $X_3$ and X4, independently of each other, are O or S; and n is 0 or 1 and optionally the enantiomers thereof. The active ingredients have advantageous pesticidal properties. They are especially suitable for the control of pests on domestic animals and livestock.

6 Claims, No Drawings

PESTICIDAL N-HETEROARYL ALPHA-ALKOXIMINO-CARBOXAMIDES

This application is a 371 of PCT/EP00/11840 filed on Nov. 27, 2000.

The present invention relates to new substituted aminoheterocyclylamides of formula

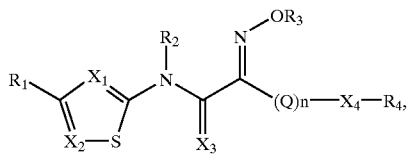

wherein $R_1$ is hydrogen, halogen, $C_1$–$C_6$-alkyl, $C_1$–$C_6$-alkoxy, $C_1$–$C_6$-haloalkyl or unsubstituted or mono- to penta-substituted phenyl, whereby the substituents are selected from the group comprising $C_1$–$C_6$-alkyl, $C_1$–$C_6$-haloalkyl, $C_1$–$C_6$-alkoxy, aryloxy, halogen, cyano and nitro, whereby if the number of substituents is greater than 1, the substituents may be identical or different;

$R_2$ is hydrogen, $C_1$–$C_6$-alkyl, ($C_1$–$C_6$-alkylene)phenyl, pyridyl, COOR$_6$, CONR$_7$R$_8$, COR$_6$, allyl or CH$_2$—O—R$_6$;

$R_3$ is $C_1$–$C_6$-alkyl;

$R_4$ is unsubstituted or substituted phenyl, unsubstituted or substituted benzyl or unsubstituted or substituted heterocyclyl, whereby each of the substituents, independently of each other, is selected from the group comprising $C_1$–$C_6$-alkyl, $C_1$–$C_6$-haloalkyl, $C_1$–$C_6$-alkoxy, aryloxy, halogen, cyano, hydroxy, amino and nitro, whereby if the number of substituents is greater than 1, the substituents may be identical or different.

$R_6$ is $C_1$–$C_6$-alkyl, phenyl or benzyl;

$R_7$ and $R_8$ independently of one another, are hydrogen or $C_1$–$C_6$-alkyl;

Q is $C_1$–$C_6$-alkylene;

$X_1$ is N or C(CN);

$X_2$ is N, C(CN), C(COOR$_6$), C(COR$_6$), C(SOR$_6$), C(CONR$_7$R$_8$) or C(NO$_2$);

$X_3$ and $X_4$, independently of each other, are O or S; and n is 0 or 1;

the preparation thereof and the use thereof in the control of pests, and also pesticides containing at least one of these compounds.

Substituted aminoheterocyclylamides having pesticidal activity are described for example in DE 197 27 162. However, the active ingredients specifically disclosed therein cannot always fulfil the requirements regarding potency and activity spectrum. There is therefore a need for active ingredients with improved pesticidal properties. It has now been found that the aminoheterocyclylamides of formula I have excellent pesticidal properties, especially against endoparasites.

The alkyl groups present in the definitions of the substituents may be straight-chained or branched and are for example methyl, ethyl, n-propyl, isopropyl, n-butyl, sec.-butyl, isobutyl, tert.-butyl, pentyl and hexyl, as well as the branched isomers thereof.

Corresponding alkylene groups may likewise be straight-chained or branched and are for example methylene, ethylene, n-propylene, isopropylene, n-butylene, sec.-butylene, isobutylene, tert.-butylene, pentylene and hexylene, as well as the branched isomers thereof.

As a rule, halogen signifies fluorine, chlorine, bromine or iodine. The same applies to halogen in combination with other significances, such as halogenalkyl or halogenphenyl.

Halogenalkyl groups preferably have a chain length of 1 to 6 carbon atoms. Halogenalkyl is for example fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a chain length of 1 to 6 carbon atoms. Alkoxy is for example methoxy, ethoxy, propoxy, isopropoxy, n-butoxy, isobutoxy, sec.-butoxy and tert.-butoxy, as well as the isomers pentyloxy and hexyloxy; preferably methoxy and ethoxy.

Heterocyclyl signifies an aliphatic or aromatic, optionally benzocondensed, threefold to eightfold, cyclic group which contains at least one hetero atom from the group comprising oxygen, nitrogen and sulphur, with five- and sixfold heterocycles being preferred. Typical representatives are, for example, dioxolanyl, pyrrolidinyl, piperidinyl, morpholinyl, pyridyl, pyrryl, furyl, thienyl, imidazolyl, tetrahydrofuryl, tetrahydropyrryl, tetrahydropyranyl, dihydrofuryl, dihydropyranyl, benzofuryl, benzothienyl, isoxazolyl, oxazolyl, thiazolyl, oxazolinyl, oxazolidinyl, indolyl, imidazolinyl, imidazolidinyl and dioxanyl.

Preferred compounds within the context of formula I are those in which $R_1$ is halogen, $C_1$–$C_6$-alkyl, $C_1$–$C_6$-alkoxy, $C_1$–$C_6$-haloalkyl or unsubstituted or mono- to penta-substituted phenyl, whereby the substituents are selected from the group comprising $C_1$–$C_6$-alkyl, $C_1$–$C_6$-haloalkyl, $C_1$–$C_6$-alkoxy, aryloxy, halogen, cyano and nitro, whereby if the number of substituents is greater than 1, the substituents may be the same or different;

$R_2$ is hydrogen, $C_1$–$C_6$-alkyl, ($C_1$–$C_6$-alkylene)phenyl or pyridyl;

$R_3$ is $C_1$–$C_6$-alkyl;

$R_4$ is unsubstituted or substituted phenyl, unsubstituted or substituted benzyl or unsubstituted or substituted heterocyclyl, whereby each of the substituents, independently of each other, is selected from the group comprising $C_1$–$C_6$-alkyl, $C_1$–$C_6$-haloalkyl, $C_1$–$C_6$-alkoxy, aryloxy, halogen, cyano, hydroxy, amino and nitro, whereby if the number of substituents is greater than 1, the substituents may be identical or different.

Q is $C_1$–$C_6$-alkylene;

$X_1$ is N or C(CN);

$X_2$ is N or C(CN);

$X_3$ and $X_4$, independently of each other, are O or S; and n is 0 or 1.

Especially preferred embodiments in the context of the compounds of formula I are:

(1) A compound of formula I, wherein $R_1$ is halogen or $C_1$–$C_6$-haloalkyl; preferably fluorine, chlorine or $C_1$–$C_4$-haloalkyl; more preferably chlorine or $C_1$–$C_2$-haloalkyl; most preferably chlorine or trifluoromethyl;

(2) A compound of formula I, wherein $R_2$ is hydrogen or $C_1$–$C_6$-alkyl; preferably hydrogen or $C_1$–$C_2$-alkyl; most preferably hydrogen;

(3) A compound of formula I, wherein $R_3$ is $C_1$–$C_4$-alkyl; preferably $C_1$–$C_2$-alkyl; most preferably methyl;

(4) A compound of formula I, wherein $R_4$ is unsubstituted or substituted heterocyclyl, whereby the substituents are selected from the group comprising $C_1$–$C_4$-alkyl, $C_1$–$C_4$-haloalkyl, $C_1$–$C_4$-alkoxy, aryloxy, halogen, cyano, hydroxy, amino and nitro, whereby if the number of substituents is greater than 1, the substituents may be identical or different; preferably unsubstituted or substituted heterocyclyl, whereby the substituents are selected from the group comprising halogen, cyano and nitro, whereby if the number of substituents is greater than 1, the substituents may be identical or different; more preferably unsubstituted or substituted heterocyclyl, whereby the substituents are selected from the group comprising fluorine, chlorine or bromine, whereby if the number of substituents is greater than 1, the substituents may be identical or different; most preferably unsubstituted or chlorine-substituted heterocycly; especially pyrrolidinyl, piperidinyl, pyridyl, pyrryl, furyl, thienyl, tetrahydrofuryl, benzofuryl or benzothienyl;

(5) A compound of formula I, wherein Q is $C_1$–$C_2$-alkylene;

(6) A compound of formula I, wherein $X_3$ is O;

(7) A compound of formula I, wherein $X_4$ is O;

(8) A compound of formula I, wherein n is 1;

(9) A compound of formula I, wherein $R_1$ is halogen or $C_1$–$C_6$-haloalkyl; $R_2$ is hydrogen or $C_1$–$C_6$-alkyl; $R_3$ is $C_1$–$C_4$-alkyl; $R_4$ is unsubstituted or substituted heterocyclyl, whereby the substituents are selected from the group comprising $C_1$–$C_4$-alkyl, $C_1$–$C_4$-haloalkyl, $C_1$–$C_4$-alkoxy, aryloxy, halogen, cyano, hydroxy, amino and nitro, whereby if the number of substituents is greater than 1, the substituents may be identical or different; Q is $C_1$–$C_2$-alkylene; $X_3$ and $X_4$ are O; and n is 1;

(10) A compound of formula I, wherein $R_1$ is fluorine, chlorine or $C_1$–$C_4$-haloalkyl; $R_2$ is hydrogen or $C_1$–$C_2$-alkyl; $R_3$ is $C_1$–$C_2$-alkyl; $R_4$ is unsubstituted or substituted heterocyclyl, whereby the substituents are selected from the group comprising halogen, cyano and nitro, whereby if the number of substituents is greater than 1, the substituents may be identical or different; Q is $C_1$–$C_2$-alkylene; $X_3$ and $X_4$ are O; and n is 1;

(11) A compound of formula I, wherein $R_1$ is chlorine or $C_1$–$C_2$-haloalkyl; $R_2$ is hydrogen; $R_3$ is methyl; $R_4$ is unsubstituted or substituted heterocyclyl, whereby the substituents are selected from the group comprising fluorine, chlorine or bromine, whereby if the number of substituents is greater than 1, the substituents may be identical or different; Q is $C_1$–$C_2$ alkylene; $X_3$ and $X_4$ are O; and n is 1;

(12) A compound of formula I, wherein $R_1$ is chlorine or trifluoromethyl; $R_2$ is hydrogen; $R_3$ is methyl; $R_4$ is unsubstituted or chlorine-substituted heterocyclyl; Q is $C_1$–$C_2$-alkylene; $X_3$ and $X_4$ are O; and n is 1;

(13) A compound of formula I, wherein $R_1$ is chlorine or trifluoromethyl; $R_2$ is hydrogen; $R_3$ is methyl; $R_4$ is pyrrolidinyl, piperidinyl, pyridyl, pyrryl, furyl, thienyl, tetrahydrofuryl, benzofuryl or benzothienyl; Q is $C_1$–$C_2$-alkylene; $X_3$ and $X_4$ are O; and n is 1.

A further object of the invention is the process for the preparation of the compounds of formula I and optionally the enantiomers thereof, for example characterised in that a compound of formula

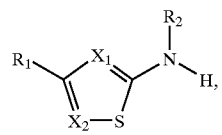

II which is known or may be produced analogously to corresponding known compounds, and wherein $R_1$, $R_2$, $X_1$ and $X_2$ are defined as given for formula I, a) is reacted with a compound of formula

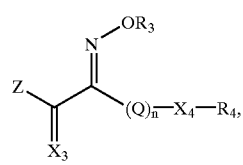

III which is known or may be prepared analogously to corresponding known compounds, and wherein $X_3$, $X_4$, $R_3$, $R_4$, n and Q are defined as for formula I and Z is a leaving group, if required in the presence of a basic catalyst, or b) is reacted with a compound of formula

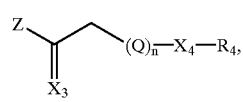

IV which is known or may be prepared analogously to corresponding known compounds, and wherein $X_4$, $R_4$, n and Q are defined as for formula I, and Z is a leaving group and $X_3$ is O, if required in the presence of a basic catalyst, the nitroso group is introduced into the resulting product, optionally after isolation thereof, and the resulting oxime, optionally after fresh isolation, is reacted with a compound of formula $R_3X_5$  V, which is known or may be prepared analogously to corresponding known compounds, and wherein $X_3$ is defined as for formula I and $X_5$ is a leaving group, if required in the presence of a basic catalyst, and the resulting product, optionally after isolation is reacted if desired with a sulphurising agent, and if desired, a compound of formula I which is obtainable by this process or in another way, or an enantiomer thereof, may be converted into another compound of formula I or an enantiomer thereof, a mixture of enantiomers which is obtainable by this process is separated and the desired enantiomer isolated.

Suitable leaving groups are halogen, $C_1$–$C_6$-alkoxy or hydroxy, preferably chlorine.

Suitable bases for facilitating the reaction are e.g. trialkylamines, basic heterocycles or phosphines. Triethylamine, diisopropylethylamine, pyridine, 4-(N,N-dimethylamino)pyridine, quinuclidine, 1,5-diazabicyclo[5.4.0]undec-5-ene (DBU) and triphenylphosphine may be mentioned by way of example. Diisopropylethylamine is preferred.

Suitable compositions for introducing the nitroso group are alkali metal nitrites, preferably sodium nitrite.

Suitable sulphurising compositions are sulphides of phosphoric acid, preferably $P_4S_{10}$.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxane; ketones such as acetone, methyl ethyl ketone or methyl isobutyl ketone; amides such as N,N-dimethylformamide, N,N-diethylformamide, N,N-dimethylacetamide, N-methylpyrrolidone or hexamethylphosphoric acid triamide; nitrites such as acetonitrile or propionitrile; and sulfoxides, such as dimethyl sulfoxide. If the reaction takes place in the presence of a base, then bases used in excess, such as triethylamine, pyridine, N-methylmorpholine, or N,N-diethylaniline, can also serve as solvents or diluents. Preferably, halogenated hydrocarbons are used, especially dichloromethane.

The reaction which introduces the nitroso group is advantageously carried out in an aqueous acid. Hydrochloric and sulphuric acid are. preferred for this, especially hydrochloric acid.

The reaction is advantageously carried out in a temperature range of ca. −20° C. to ca. +150° C., preferably from ca. −10° C. to ca. +80° C., most preferably from ca. 0° C. to ca. +40° C.

In a preferred embodiment, a compound of formula II is reacted at 0° to 120°, preferably 20°, in a halogenated hydrocarbon, preferably dichloromethane, with a compound of formula III.

The compounds I may be present in the form of one of the possible isomers or as a mixture thereof, e.g. depending on the number, absolute and relative configurations of the asymmetric carbon atoms as pure isomers, such as antipodes and/or diastereoisomers, or as isomeric mixtures, such as enantiomeric mixtures, e.g. racemates, diastereoisomeric mixtures or racemic mixtures; the invention relates to both the pure isomers and all the possible isomeric mixtures, and is to be understood as such hereinbefore and hereinafter, even if stereochemical details are not specifically mentioned in each case.

Depending on the choice of starting materials and procedures, diastereoisomeric mixtures and racemic mixtures of compounds 1, which are obtained in accordance with the invention or in another way, may be separated in known manner into the pure diastereoisomers or racemates based on the physical-chemical differences of the constituents, for example by means of fractional crystallisation, distillation and/or chromatography.

Mixtures of enantiomers that are obtainable accordingly, such as racemates, may be broken down into the optical antipodes by known methods, for example by recrystallisation from an optically active solvent, by chromatography on chiral adsorbents, e.g. high-pressure liquid chromatography (HPLC) on acetyl cellulose, with the assistance of appropriate microorganisms, by cleavage with specific immobilised enzymes, through the formation of inclusion compounds, e.g. using chiral crown ethers, wherein only one enantiomer is complexed.

According to the invention, apart from isolation of corresponding isomer mixtures, generally known methods of diastereoselective or enantioselective synthesis can also be applied to obtain pure diastereoisomers or enantiomers, e.g. by carrying out the method of the invention using educts with correspondingly suitable stereochemistry.

It is advantageous to isolate or synthesize the biologically more active isomer in each case, e.g. enantiomer or isomer mixture, e.g. enantiomer mixture, if the individual components show differences in biological efficacy.

In the method of the present invention, the starting materials and intermediates used are preferably those that lead to the compounds I described at the beginning as being especially useful.

The invention relates especially to the method of preparation described in the example.

Starting materials and intermediates, which are new and are used according to the invention for the preparation of compounds I, as well as their usage and process for the preparation thereof, similarly form an object of the invention.

The compounds I according to the invention are notable for their broad activity spectrum and are valuable active ingredients for use in pest control, including in particular the control of endo- and ecto-parasites on animals, whilst being well-tolerated by warm-blooded animals, fish and plants, In the context of the present invention, ectoparasites are understood to be in particular insects, mites and ticks. These include insects of the order: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga camaria, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Stomoxys calcitrans, Haematobia irritans* and midges (Nematocera), such as Culicidae, Simuliidae, Psychodidae, but also blood-sucking parasites, for example fleas, such as *Ctenocephalides felis* and *Ctenocephalides canis* (cat and dog fleas), *Xernopsylla cheopis, Pulex irritans, Dermatophilus penetrans*, lice, such as *Damalina ovis, Pediculus humanis*, biting flies and horse-flies (Tabanidae), Haematopota spp. such as *Haematopota pluvialis*, Tabanidea spp. such as *Tabanus nigrovittatus*, Chrysopsinae spp. such as *Chrysops caecutiens*, tsetse flies, such as species of Glossinia, biting insects, particularly cockroaches, such as *Blatella germanica, Blatta orientalis, Periplaneta americana*, mites, such as *Dermanyssus gallinae, Sarcoptes scabiei, Psoroptes ovis* and Psorergates spp. and last but not least ticks. The latter belong to the order Acarina. Known representatives of ticks are, for example, Boophilus, Amblyomma, Anocentor, Dermacentor, Haemaphysalis, Hyalomma, Ixodes, Rhipicentor, Margaropus, Rhipicephalus, Argas, Otobius and Omithodoros and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

Compounds I can also be used against hygiene pests, especially of the order Diptera of the families Sarcophagidae, Anophilidae and Culicidae; the orders Orthoptera, Dictyoptera (e.g. the family Blattidae) and Hymenoptera (e.g. the family Formicidae).

Compounds I also have sustainable efficacy on parasitic mites and insects of plants. In the case of spider mites of the order Acarina, they are effective against eggs, nymphs and adults of Tetranychidae (Tetranychus spp. and Panonychus spp.).

They have high activity against sucking insects of the order Homoptera, especially against pests of the families Aphididae, Delphacidae, Cicadellidae, Psyllidae, Loccidae, Diaspididae and Eriophydidae (e.g. rust mite on citrus fruits); the orders Hemiptera, Heteroptera and Thysanoptera, and on the plant-eating insects of the orders Lepidoptera, Coleoptera, Diptera and Orthoptera.

They are similarly suitable as a soil insecticide against pests in the soil.

The compounds of formula I are therefore effective against all stages of development of sucking insects and eating insects on crops such as cereals, cotton, rice, maize, soya, potatoes, vegetables, fruit, tobacco, hops, citrus, avocados and other crops.

The compounds of formula I are also effective against plant nematodes of the species Meloidogyne, Heterodera, Pratylenchus, Ditylenchus, Radopholus, Rizoglyphus etc.

In particular, the compounds are effective against helminths, in which the endoparasitic nematodes may be the cause of serious diseases of mammals and poultry, e.g. sheep, pigs, goats, cattle, horses, donkeys, dogs, cats, guinea-pigs and exotic birds. Typical nematodes of this indication are: Haemonchus, Trichostrongylus, Ostertagia, Nematodirus, Cooperia, Ascadis, Bunostonum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris and Parascadis. The particular advantage of the compounds of formula I is their efficacy against those parasites that are resistant towards active ingredients based on benzimidazole.

Certain pests of the species Nematodirus, Cooperia and Oesophagostonum infest the intestinal tract of the host animal, while others of the species Haemonchus and Ostertagia are parasitic in the stomach and those of the species Dictyocaulus are parasitic in the lung tissue. Parasites of the families Filaridae and Setariidae may be found in the internal cell tissue and in the organs, e.g. the heart, the blood vessels, the lymph vessels and the subcutaneous tissue. A particularly notable parasite is the heartworm of the dog, *Dirofilaria immitis*. The compounds of formula I are highly effective against these parasites.

Furthermore, the compounds of formula I are also especially suitable for the control of human pathogenic parasites. Of these, typical representatives that appear in the digestive tract are those of the species Ancylostoma, Necator, Ascads, Strongyloides, Trichinella, Capillara, Trichuris and Enterobius. The compounds of the present invention are also effective against parasites of the species Wuchereria, Brugia, Onchocerca and Loa from the family of Filariidae, which appear in the blood, in the tissue and in various organs, and also against Dracunculus and parasites of the species Strongyloides and Trichinella, which infect the gastrointestinal tract in particular.

The good pesticidal activity of the compounds of formula I corresponds to a mortality rate of at least 50–60% of the pests mentioned. In particular, the compounds of formula I are notable for the exceptionally long duration of efficacy.

The activity of the compounds according to the invention and of the compositions containing them against animal pests may be substantially broadened and adapted to the prevailing circumstances by adding other insecticides and/or acaricides. The additives in question may be for example representatives of the following classes of active ingredient: organophosphorus compounds, nitrophenols and derivatives, formamidines, ureas, carbamates, pyrethroids, chlorinated hydrocarbons, neonicotinoids and *Bacillus thuringiensis* preparations.

The compounds of formula I are preferably employed in unmodified form or preferably together with the adjuvants conventionally used in the art of formulation and may therefore be processed in a known manner to give, for example, emulsifiable concentrates, directly sprayable or dilutable solutions, dilute emulsions, wettable powders, soluble powders, dusts, granules or microencapsulations in polymeric substances. As with the compositions, the methods of application, such as spraying, atomizing, dusting, scattering or pouring, are selected in accordance with the intended objectives and the prevailing circumstances.

The formulation, i.e. the agents, preparations or compositions containing the active ingredient of formula I, or combinations of these active ingredients with other agrochemical active ingredients, and optionally a solid or liquid adjuvant, are produced in a manner known per se, for example by intimately mixing and/or grinding the active ingredients with spreading compositions, for example with solvents, solid carriers, and optionally surface-active compounds (surfactants).

The solvents in question may be: aromatic hydrocarbons, preferably fractions of alkylbenzenes having 8 to 12 carbon atoms, such as xylene mixtures or alkylated naphthalenes, aliphatic or cyclo-aliphatic hydrocarbons, such as cyclohexane, paraffins or tetrahydronaphthalene, alcohols, such as ethanol, propanol or butanol, glycols and their ethers and esters, such as propylene glycol, dipropylene glycol ether, ethylene glycol or ethylene glycol monomethyl or -ethyl ether, ketones, such as cyclohexanone, isophorone or diacetanol alcohol, strong polar solvents, such as N-methyl-2-pyrrolidone, dimethyl sulfoxide or dimethylformamide, or water, vegetable oils, such as rape, castor, coconut, or soybean oil, and also, if appropriate, silicone oils.

The solid carriers used for example for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable non-sorbent carriers are materials such as calcite or sand. In addition, a great number of pregranulated materials of inorganic or organic nature can be used, e.g. especially dolomite or pulverised plant residues.

Depending on the type of active ingredient of formula I to be formulated, or the combination of these active ingredients with other insecticides or acaricides, suitable surface-active compounds are non-ionic, cationic and/or anionic surfactants having good emulsifying, dispersing and wetting properties. The surfactants are also understood to be surfactant mixtures.

Suitable anionic surfactants can be both so-called water-soluble soaps and water-soluble synthetic surfactant compounds.

Suitable soaps are the alkali metal salts, alkaline earth metal salts or unsubstituted or substituted ammonium salts of higher fatty acids ($C_{10}$–$C_{22}$), for example the sodium or potassium salts of oleic or stearic acid, or of natural fatty acid mixtures which can be obtained for example from coconut oil or tallow oil. The fatty acid methyltaurine salts may also be mentioned as surfactants.

More frequently, however, so-called synthetic surfactants are used, especially fatty sulphonates, fatty sulphates, sulphonated benzimidazole derivatives or alkylarylsulphonates.

The fatty sulphonates or sulphates are usually in the form of alkali metal salts, alkaline earth metal salts or unsubstituted or substituted ammoniums salts and have an alkyl radical with 8 to 22 carbon atoms, which also includes the alkyl moiety of acyl radicals, for example, the sodium or calcium salt of ligninsulphonic acid, of dodecylsulphate or of a mixture of fatty alcohol sulphates obtained from natural fatty acids. These compounds also comprise the salts of sulphuric acid esters and sulphonic acids of fatty alcoholethylene oxide adducts. The sulphonated benzimidazole derivatives preferably contain 2 sulphonic acid groups and one fatty acid radical containing 8 to 22 carbon atoms. Examples of alkylarylsulfonates are the sodium, calcium or triethanolamine salts of dodecylbenzenesulphonic acid, dibutyinapthalenesulphonic acid, or of a naphthalenesulphonic acid/formaldehyde condensation product. Also suitable are corresponding phosphates, e.g. salts of the phosphoric acid ester of an adduct of p-nonylphenol with 4 to 14 moles of ethylene oxide or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediamine polypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Also suitable are fatty acid esters of polyoxyethylene sorbitan, such as polyoxyethylene sorbitan trioleate.

Cationic surfactants are preferably quaternary ammonium salts which have as N-substituent at least one $C_8$–$C_{22}$ alkyl radical and, as further substituents, lower—where appropriate—halogenated alkyl, benzyl or lower hydroxyalkyl radicals. The salts preferably exist as halides, methyl sulphates or ethyl sulphates, preferably as stearyl trimethylammonium chloride or benzyl-di-(2-chloroethyl)-ethylammonium bromide.

The surfactants which are customary in formulation technology are described for example in the following publications:

"Mc Cutcheon's Detergents and Emulsifiers Annual", McPublishing Corp., Glen Rock, N.J., USA, 1988", H. Stache, "Tensid-Taschenbuch" (Surfactants Handbook), $2^{nd}$ edition, C. Hanser Publishing Munich, Vienna 1981.

M. and J. Ash. "Encyclopedia of Surfactants", Vol. I–III, Chemical Publishing Co., New York, 1980–1981.

Preferred application forms for usage on warm-blooded animals in the control of helminths include solutions, emulsions, suspensions (drenches), food additives, powders, tablets including effervescent tablets, boli, capsules, microcapsules and pour-on formulations, whereby the physiological compatability of the formulation excipients must be taken into consideration.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), glidants and disintegrants.

If the anthelminthics are present in the form of feed concentrates, then the carriers used are e.g. performance feeds, feed grain or protein concentrates. Such feed concentrates or compositions may contain, apart from the active ingredients, also additives, vitamins, antibiotics, chemotherapeutics or other pesticides, primarily bacteriostats, fungistats, coccidiostats, or even hormone preparations, substances having anabolic action or substances which promote growth, which affect the quality of meat of animals for slaughter or which are beneficial to the organism in another way. If the compositions or the active ingredients of formula I contained therein are added directly to feed or to the drinking troughs, then the formulated feed or drink contains the active ingredients preferably in a concentration of ca. 0.0005 to 0.02% by weight (5–200 ppm).

Application of the compositions according to the invention to the animals to be treated may take place topically, perorally, parenterally or subcutaneously, the composition being present in the form of solutions, emulsions, suspensions, (drenches), powders, tablets, boli, capsules and pour-on formulations.

The compounds of formula I according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. If the range of activity is to be extended to endoparasites, e.g. wormers, the compounds of formula I are suitably combined with substances having endoparasitic properties. Of course, they can also be used in combination with antibacterial compositions. Since the compounds of formula I are adulticides, i.e. since they are effective in particular against the adult stage of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula I.

Suitable partners in the mixture may be biocides, e.g. the insecticides and acaricides with a varying mechanism of activity, which are named in the following and have been known to the person skilled in the art for a long time, e.g.

chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers.

Non-limiting examples of suitable insecticides and acaricides are:

| | | | | | |
|---|---|---|---|---|---|
| (I) | Aldicarb; | | | | |
| (II) | Azinphos-methyl; | (XVI) | Diflubenzuron; | (XXXV) | Teflubenzuron; |
| | | (XVII) | Endosulfan; | (XXXVI) | Terbufos; |
| (III) | Benfuracarb; | (XVIII) | Ethiofencarb; | (XXXVII) | Triazamate; |
| (IV) | Bifenthrin; | (XIX) | Fenitrothion; | (XXXVIII) | Abamectin; |
| (V) | Buprofezin; | (XX) | Fenobucarb; | (XXXIX) | Fenobucarb; |
| (VI) | Carbofuran; | (XXI) | Fenvalerate; | (XL) | Tebufenozide; |
| (VII) | Dibutylaminothio; | (XXII) | Formothion; | (XLI) | Fipronil; |
| | | (XXIII) | Methiocarb; | (XLII) | beta-Cyfluthrin; |
| (VIII) | Cartap; | (XXIV) | Heptenophos; | (XLIII) | Silafluofen; |
| (IX) | Chlorfluazuron; | (XXV) | Imidacloprid; | (XLIV) | Fenpyroximate; |
| (X) | Chlorpyrifos; | (XXVI) | Isoprocarb; | (XLV) | Pyridaben; |
| (XI) | Cyfluthrin; | (XXVII) | Methamidophos; | (XLVI) | Fenazaquin; |
| (XII) | Lambda-Cyhalothrin; | (XXVIII) | Methomyl; | (XLVII) | Pyriproxyfen; |
| | | (XXIX) | Mevinphos; | (XLVIII) | Pyrimidifen; |
| (XIII) | Alpha-cypermethrin; | (XXX) | Parathion; | (XLIX) | Nitenpyram; |
| | | (XXXI) | Parathionmethyl; | (L) | Ni-25, Acetamiprid; |
| (XIV) | zeta-Cypermethrin; | (XXXII) | Phosalone; | | |
| | | (XXXIII) | Pirimicarb; | | |
| (XV) | Deltamethrin; | (XXXIV) | Propoxur; | | |
| (LII) | Avermectin $B_1$; | | | | |
| (LIII) | an insect-active extract from a plant; | | | | |
| (LIV) | a preparation containing insect-active nematodes; | | | | |
| (LV) | a preparation obtained from *Bacillus subtilis*; | | | | |
| (LVI) | a preparation containing insect-active fungi; | | | | |
| (LVII) | a preparation containing insect-active viruses; | | | | |
| (LIX) | AC 303 630; | (LXVIII) | Azocyclotin; | (LXXVII) | Butylpyridaben; |
| (LX) | Acephat; | (LXIX) | Bendiocarb; | (LXXVIII) | Cadusafos; |
| (LXI) | Acrinathrin; | (LXX) | Bensultap; | (LXXIX) | Carbaryl; |
| (LXII) | Alanycarb; | (LXXI) | Betacyfluthrin; | (LXXX) | Carbophenthion; |
| (LXIII) | Alphamethrin; | (LXXII) | BPMC; | (LXXXI) | Chloethocarb; |
| (LXIV) | Amitraz; | (LXXIII) | Brofenprox; | (LXXXII) | Chlorethoxyfos; |
| (LXV) | Az 60541; | (LXXIV) | Bromophos A; | (LXXXIII) | Chlormephos; |
| (LXVI) | Azinphos A; | (LXXV) | Bufencarb; | (LXXXIV) | Cis-Resmethrin; |
| (LXVII) | Azinphos M; | (LXXVI) | Butocarboxin; | (LXXXV) | Clocythrin; |
| (LXXXVI) | Clofentezin; | (CXVIII) | Fosthiazat; | (CLI) | Prothoat; |
| (LXXXVII) | Cyanophos; | (CXIX) | Fubfenprox; | (CLII) | Pyrachlophos; |
| (LXXXVIII) | Cycloprothrin; | (CXX) | HCH; | (CLIII) | Pyradaphenthion; |
| (LXXXIX) | Cyhexatin; | (CXXI) | Hexaflumuron; | | |
| (XC) | Demeton M; | (CXXII) | Hexythiazox; | (CLIV) | Pyresmethrin; |
| (XCI) | Demeton S; | (CXXIII) | Iprobenfos; | (CLV) | Pyrethrum; |
| (XCII) | Demeton-S-methyl; | (CXXIV) | Isofenphos; | (CLVI) | RH 5992; |
| | | (CXXV) | Isoxathion; | (CLVII) | Salithion; |
| (XCIII) | Dichlofenthion; | (CXXVI) | Ivermectin; | (CLVIII) | Sebutos; |
| (XCIV) | Dicliphos; | (CXXVII) | Lambda-cyhalothrin; | (CLIX) | Sultotep; |
| (XCV) | Diethion; | | | (CLX) | Sulprofos; |
| (XCVI) | Dimethoat; | (CXXVIII) | Matathion; | (CLXI) | Tebufenpyrad; |
| (XCVII) | Dimethylvinphos; | (CXXIX) | Mecarbam; | (CLXII) | Tebupirimphos; |
| | | (CXXX) | Mesulfenphos; | (CLXIII) | Tefluthrin; |
| (XCVIII) | Dioxathion; | (CXXXI) | Metaldehyd; | (CLXIV) | Temephos; |
| (XCIX) | Edifenphos; | (CXXXII) | Metolcarb; | (CLXV) | Terbam; |
| (C) | Emamectin; | (CXXXIII) | Milbemectin; | (CLXVI) | Tetrachlorvinphos; |
| (CI) | Esfenvalerat; | (CXXXIV) | Moxidectin; | | |
| (CII) | Ethion; | (CXXXV) | Naled; | (CLXVII) | Thiafenox; |
| (CIII) | Ethofenprox; | (CXXXVI) | NC 184; | (CLXVIII) | Thiodicarb; |
| (CIV) | Ethoprophos; | (CXXXVII) | Omethoat; | (CLXIX) | Thiofanox; |
| (CV) | Etrimphos; | (CXXXVIII) | Oxamyl; | (CLXX) | Thionazin; |
| (CVI) | Fenamiphos; | (CXXXIX) | Oxydemethon M; | (CLXXI) | Thuringiensin; |
| (CVII) | Fenbutatinoxid; | (CXL) | Oxydeprofos; | (CLXXII) | Tralomethrin; |
| (CVIII) | Fenothiocarb; | (CXLI) | Permethrin; | (CLXXIII) | Triarthen; |
| (CIX) | Fenpropathrin; | (CXLII) | Phenthoat; | (CLXXIV) | Triazophos; |
| (CX) | Fenpyrad; | (CXLIII) | Phorat; | (CLXXV) | Triazuron; |
| (CXI) | Fenthion; | (CXLIV) | Phosmet; | (CLXXVI) | Trichlorfon; |
| (CXII) | Fluazinam; | (CXLV) | Phoxim; | (CLXXVII) | Triflumuron; |
| (CXIII) | Flucycloxuron; | (CXLVI) | Pirimiphos M; | (CLXXVIII) | Trimethacarb; |
| (CXIV) | Flucythrinat; | (CXLVII) | Pirimiphos A; | (CLXXIX) | Vamidothion; |
| (CXV) | Flufenoxuron; | (CXLVIII) | Promecarb; | (CLXXX) | Xylylcarb; |
| (CXVI) | Flufenprox; | (CXLIX) | Propaphos; | (CLXXXI) | YI 5301/5302; |
| (CXVII) | Fonophos; | (CL) | Prothiofos; | (CLXXXII) | Zetamethrin; |
| (CLXXXIII) | DPX-MP062; | | | | |
| (CLXXXIV) | RH-2485; | | | | |
| (CLXXXV) | D 2341; | | | | |

| | |
|---|---|
| (CLXXXVI) | XMC (3,5,-Xy-lyl-Methyl carbamat), |
| (CLXXXVII) | Lutenuron |
| (CLXXXVIII) | Fluazuron |
| (CLXXXIX) | Methoprene |
| (CXC) | Hydroprene |
| (CXCI) | Fenoxycarb |
| (CXCII) | Chlorfenapyr or |
| (CXCIII) | Spinosad |

Non-limitative examples of suitable anthelminthics are named in the following, a few representatives have insecticidal and acaricidal activity in addition to the anthelminthic activity, and are partly already in the above list.
(A1) Praziquantel=2-cyclohexylcarbonyl-4-oxo-1,2,3,6,7, 11b-hexahydro-4H-pyrazino[2,1-α]isoquinoline
(A2) Closantel=3,5-diiodo-N-[5-chloro-2-methyl-4-(a-cyano-4-chlorobenzyl)phenyl]salicylamide
(A3) Triclabendazole=5-chloro-6-(2,3-dichlorophenoxy)-2-methylthio-1H-benzimidazole
(A4) Levamisol=L-(−)-2,3,5,6-tetrahydro-6-phenylimidazo [2,1b]thiazole
(A5) Mebendazole=(5-benzoyl-1H-benzimidazol-2-yl) carbaminic acid methylester
(A6) Omphalotin=a macrocyclic fermentation product of the fungus *Omphalotus olearius* described in WO 97/20857
(A7) Abamectin=avermectin B1
(A8) Ivermectin=22,23-dihydroavermectin B1
(A9) Moxidectin=5-O-demethyl-28-deoxy-25-(1,3-dimethyl-1-butenyl)-6,28-epoxy-23-(methoxyimino)-milbemycin B
(A10) Doramectin=25-cyclohexyl-5-O-demethyl-25-de(1-methylpropyl)-avermectin A1a
(A11) Milbemectin=mixture of milbemycin A3 and milbemycin A4
(A12) Milbemycinoxim=5-oxim of milbemectin Non-limitative examples of suitable repellents and detachers are:
(R1) DEET (N,N-diethyl-m-toluamide)
(R2) KBR 3023 N-butyl-2-oxycarbonyl-(2-hydroxy)-piperidine
(R3) Cymiazole=N,-2,3-dihydro-3-methyl-1,3-thiazol-2-ylidene-2,4-xylidene The said partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature. Therefore, the following listing is restricted to a few places where they may be found by way of example.
(I) 2-Methyl-2-(methylthio)propionaldehyd-O-Methylcarbamoyloxime (Aldicarb), from The Pesticide Manual, $11^{th}$Ed. (1997), The British Crop Protection Council, London, page 26;
(II) S(3,4-Dihydro-4-oxobenzo[d]-[1,2,3]-triazin-3-ylmethyl)O,O-dimethyl-phosphorodithioate (Azinphosmethyl), from The Pesticide Manual, $11^{th}$Ed. (1997), The British Crop Protection Council, London, page 67;
(III) Ethyl-N-[2,3-dihydro-2,2-dimethylbenzofuran-7-yloxycarbonyl-(methyl)aminothio]-N-isopropyl-β-alaninate (Benfuracarb), from The Pesticide Manual, $11^{th}$Ed. (1997), The British Crop Protection Council, London, page 96;
(IV) 2-Methylbiphenyl-3-ylmethyl-(Z)-(1RS)-cis-3-(2-chlor-3,3,3-trifluorprop-1-enyl)-2,2-dimethylcyclopropancarboxylate (Bifenthrin), from The Pesticide Manual, $11^{th}$Ed. (1997), The British Crop Protection Council, London, page 118;
(V) 2-tert-Butylimino-3-isopropyl-5-phenyl-1,3,5-thiadiazian-4-one (Buprofezin), from The Pesticide Manual, $11^{th}$Ed. (1997), The British Crop Protection Council, London, page 157;
(VI) 2,3-Dihydro-2,2-dimethylbenzofuran-7-yl-methylcarbamate (Carbofuran), from The Pesticide Manual, $11^{th}$Ed. (1997), The British Crop Protection Council, London, page 186;
(VII) 2,3-Dihydro-2,2-dimethylbenzofuran-7-yl-(dibutylaminothio)methylcarbamate (Carbosulfan), from The Pesticide Manual, $11^{th}$Ed. (1997), The British Crop Protection Council, London, page 188;
(VIII) S,S'-(2-Dimethylaminotrimethylene)-bis (thiocarbamate) (Cartap), from The Pesticide Manual, $11^{th}$Ed. (1997), The British Crop Protection Council, London, page 193;
(IX) 1-[3,5-Dichloro-4-(3-chloro-5-trifluoromethyl-2-pyridyloxy)phenyl]-3-(2,6-difluorobenzoyl)-urea (Chlorfluazuron), from The Pesticide Manual, $11^{th}$Ed. (1997), The British Crop Protection Council, London, page 213;
(X) O,O-Diethyl-O-3,5,6-trichloro-2-pyridyl-phosphorothioate (Chlorpyrifos), from The Pesticide Manual, $11^{th}$Ed. (1997), The British Crop Protection Council, London, page 235;
(XI) (RS)-α-Cyano-4-fluoro-3-phenoxybenzyl-(1RS, 3RS;1RS,3RS)-3-(2,2-dichlorovinyl)-2,2-dimethylcyclopropancarboxylate (Cyfluthrin), from The Pesticide Manual, $11^{th}$Ed. (1997), The British Crop Protection Council, London, page 293;
(XII) Mixture of (S)-α-Cyano-3-phenoxybenzyl-(Z)-(1R, 3R)-3-(2-chloro-3,3,3-trifluoropropenyl)-2,2-dimethylcyclopropanecarboxylate and (R)-α-cyano-3-phenoxybenzyl-(Z)-(1R,3R)-3-(2-chloro-3,3,3-trfluoropropenyl)-2,2-dimethylcyclopropanecarboxylate (Lambda-Cyhalothrin), from The Pesticide Manual, $11^{th}$Ed. (1997), The British Crop Protection Council, London, page 300;
(XIII) Racemate consisting of (S)-α-cyano-3-phenoxybenzyl-(1R,3R)-3-(2,2-dichlorovinyl)-2,2-dimethylcyclopropanecarboxylate and (R)-α-cyano-3-phenoxybenzyl-(1 S,3S)-3-(2,2-dichlorovinyl)-2,2-dimethylcyclopropanecarboxylate (Alpha-cypermethrin), from The Pesticide Manual, $11^{th}$Ed. (1997), The British Crop Protection Council, London, page 308;
(XIV) Mixture of the stereoisomers of (S)-α-cyano-3-phenoxybenzyl(1RS,3RS,1RS,3RS)-3-(2,2-dichlorovinyl)-2,2-dimethylcyclopropanecarboxylate (zeta-Cypermethrin), from The Pesticide Manual, $11^{th}$Ed. (1997), The British Crop Protection Council, London, page 314;

(XV) (S)-α-cyano-3-phenoxybenzyl-(1R,3R)-3-(2,2-dibromovinyl)-2,2-dimethylcyclopropanecarboxylate (Deltamethrin), from The Pesticide Manual, 11$^{th}$Ed. (1997), The British Crop Protection Council, London, page 344;

(XVI) (4-Chlorophenyl)-3-(2,6-difluorobenzoyl)urea (Diflubenzuron), from The Pesticide Manual, 11$^{th}$Ed. (1997), The British Crop Protection Council, London, page 395;

(XVII) (1,4,5,6,7,7-Hexachloro-8,9,10-trinorborn-5-en-2,3-ylenbismethylene)-sulphite (Endosulfan), from The Pesticide Manual, 11$^{th}$Ed. (1997), The British Crop Protection Council, London, page 459;

(XVIII) α-Ethylthio-o-tolyl-methylcarbamate (Ethiofencarb), from The Pesticide Manual, 11$^{th}$Ed. (1997), The British Crop Protection Council, London, page 479;

(XIX) O,O-Dimethyl-O-4-nitro-m-tolyl-phosphorothioate (Fenitrothion), from The Pesticide Manual, 11$^{th}$Ed. (1997), The British Crop Protection Council, London, page 514;

(XX) 2-sec-Butylphenyl-methylcarbamate (Fenobucarb), from The Pesticide Manual, 11$^{th}$Ed. (1997), The British Crop Protection Council, London, page 516;

(XXI) (RS)-α-Cyano-3-phenoxybenzyl-(RS)-2-(4-chlorophenyl)-3-methylbutyrate (Fenvalerate), from The Pesticide Manual, 11$^{th}$Ed. (1997), The British Crop Protection Council, London, page 539;

(XXII) S-[Formyl(methyl)carbamoylmethyl]-O,O-dimethyl-phosphorodithioate (Formothion), from The Pesticide Manual, 11$^{th}$Ed. (1997), The British Crop Protection Council, London, page 625;

(XXIII) 4-Methylthio-3,5-xylyl-methylcarbamate (Methiocarb), from The Pesticide Manual, 11$^{th}$Ed. (1997), The British Crop Protection Council, London, page 813;

(XXIV) 7-Chlorbicyclo[3.2.0]hepta-2,6-dien-6-yl-dimethylphosphate (Heptenophos), from The Pesticide Manual, 11$^{th}$Ed. (1997), The British Crop Protection Council, London, page 670;

(XXV) 1-(6-Chloro-3-pyridylmethyl)-N-nitroimidazolidin-2-ylidenamine (Imidacloprid), from The Pesticide Manual, 11$^{th}$Ed. (1997), The British Crop Protection Council, London, page 706;

(XXVI) 2-Isopropylphenyl-methylcarbamate (Isoprocarb), from The Pesticide Manual, 11$^{th}$Ed. (1997), The British Crop Protection Council, London, page 729;

(XXVII) O,S-Dimethyl-phosphoramidothioate (Methamidophos), from The Pesticide Manual, 11$^{th}$Ed. (1997), The British Crop Protection Council, London, page 808;

(XXVIII) S-Methyl-N-(methylcarbarboyloxy) thioacetimidate (Methomyl), from The Pesticide Manual, 11$^{th}$Ed. (1997), The British Crop Protection Council, London, page 815;

(XXIX) Methyl-3-(dimethoxyphosphinoyloxy)but-2-enoate (Mevinphos), from The Pesticide Manual, 11$^{th}$Ed. (1997), The British Crop Protection Council, London, page 844;

(XXX) O,O-Diethyl-O-4-nitrophenyl-phosphorothioate (Parathion), from The Pesticide Manual, 11$^{th}$Ed. (1997), The British Crop Protection Council, London, page 926;

(XXXI) O,O-Dimethyl-O-4-nitrophenyl-phosphorothioate (Parathion-methyl), from The Pesticide Manual, 11$^{th}$Ed. (1997), The British Crop Protection Council, London, page 928;

(XXXII) S-6-Chloro-2,3-dihydro-2-oxo-1,3-benzoxazol-3-ylmethyl-O,O-diethyl-phosphordithioate (Phosalone), from from The Pesticide Manual, 11$^{th}$Ed. (1997), The British Crop Protection Council, London, page 963;

(XXXIII) 2-Dimethylamino-5,6-dimethylpyrimidin-4-yl-dimethylcarbamate (Pirimicarb), from The Pesticide Manual, 11$^{th}$Ed. (1997), The British Crop Protection Council, London, page 985;

(XXXIV) 2-Isopropoxyphenyl-methylcarbamate (Propoxur), from The Pesticide Manual, 11$^{th}$Ed. (1997), The British Crop Protection Council, London, page 1036;

(XXXV) 1-(3,5-Dichloro-2,4-difluorophenyl)-3-(2,6-difluorobenzoyl)urea (Teflubenzuron), from The Pesticide Manual, 11$^{th}$Ed. (1997), The British Crop Protection Council, London, page 1158;

(XXXVI) S-tert-butylthiomethyl-O,O-dimethyl-phosphorodithioate (Terbufos), from The Pesticide Manual, 11$^{th}$Ed. (1997), The British Crop Protection Council, London, page 1165;

(XXXVII) Ethyl-(3-tert.-butyl-1-dimethylcarbamoyl-1H-1,2,4-triazol-5-yl-thio)-acetate, (Triazamate), from The Pesticide Manual, 11$^{th}$Ed. (1997), The British Crop Protection Council, London, page 1224;

(XXXVIII) Abamectin, from The Pesticide Manual, 11$^{th}$Ed. (1997), The British Crop Protection Council, London, page 3;

(XXXIX) 2-sec-butylphenyl-methylcarbamate (Fenobucarb), from The Pesticide Manual, 11$^{th}$Ed. (1997), The British Crop Protection Council, London, page 516;

(XL) N-tert.-butyl-N-(4-ethylbenzoyl)-3,5-dimethylbenzohydrazide (Tebufenozide), from The Pesticide Manual, 11$^{th}$Ed. (1997), The British Crop Protection Council, London, page 1147;

(XLI) (±)-5-Amino-1-(2,6-dichloro-α,α,α-trifluoro-p-tolyl)-4-trifluoromethyl-sulphinylpyrazol-3-carbonitrile (Fipronil), from The Pesticide Manual, 11$^{th}$Ed. (1997), The British Crop Protection Council, London, page 545;

(XLII) (RS)-α-cyano-4-fluoro-3-phenoxybenzyl(1RS,3RS;1RS,3RS-3-(2,2-dichlorovinyl)-2,2-dimethylcyclopropanecarboxylate (beta-Cyfluthrin), from The Pesticide Manual, 11$^{th}$Ed. (1997), The British Crop Protection Council, London, page 295;

(XLIII) (4-Ethoxyphenyl)-[3-(4-fluoro-3-phenoxyphenyl)propyl](dimethyl)silane (Silafluofen), from The Pesticide Manual, 11$^{th}$Ed. (1997), The British Crop Protection Council, London, page 1105;

(XLIV) tert.-butyl (E)-α-(1,3-dimethyl-5-phenoxypyrazol-4-yl-methylenamino-oxy)-p-toluate (Fenpyroximate), from The Pesticide Manual, 11$^{th}$Ed. (1997), The British Crop Protection Council, London, page 530;

(XLV) 2-tert.-butyl-5-(4-tert.-butylbenzylthio)-4-chloropyridazin-3(2H)-one (Pyridaben), from The Pesticide Manual, 11$^{th}$Ed. (1997), The British Crop Protection Council, London, page 1161;

(XLVI) 4-[[4-(1,1-dimethylphenyl)phenyl]ethoxy]-quinazoline (Fenazaquin), from The Pesticide Manual, 11$^{th}$Ed. (1997), The British Crop Protection Council, London, page 507;

(XLVII) 4-Phenoxyphenyl-(RS)-2-(pyridyloxy)propyl-ether (Pyriproxyfen), from The Pesticide Manual, 11$^{th}$Ed. (1997), The British Crop Protection Council, London, page 1073;

(XLVIII) 5-Chloro-N{2-[4-(2-ethoxyethyl)-2,3-dimethylphenoxy]ethyl}-6-ethylpyrimidin-4-amine (Pyrimidifen), from The Pesticide Manual, 11$^{th}$Ed. (1997), The British Crop Protection Council, London, page 1070;

(XLIX) (E)-N-(6-chloro-3-pyrdylmethyl)-N-ethyl-N'-methyl-2-nitrovinylidenediamine (Nitenpyram), from The Pesticide Manual, 11$^{th}$Ed. (1997), The British Crop Protection Council, London, page 880;

(L) (E)-N$^1$-[(6-chloro-3-pyridyl)methyl]-N$^2$-cyano-N$^1$-methylacetamidine (NI-25, Acetamiprid), from The Pesticide Manual, 11$^{th}$Ed. (1997), The British Crop Protection Council, London, page 9;

(LI) Avermectin B$_1$, from The Pesticide Manual, 11$^{th}$Ed. (1997), The British Crop Protection Council, London, page 3;

(LII) an insect-active extract from a plant, especially (2R,6aS,12aS)-1,2,6,6a,12,12a-hexhydro-2-isopropenyl-8,9-dimethoxy-chromeno[3,4-b]furo[2,3-h]chromen-6-one (Rotenone), from The Pesticide Manual, 11$^{th}$Ed. (1997), The British Crop Protection Council, London, page 1097; and an extract from *Azadirachta indica*, especially azadirachtin, from The Pesticide Manual, 11$^{th}$Ed. (1997), The British Crop Protection Council, London, page 59; and (LIII) a preparation which contains insect-active nematodes, preferably *Heterorhabditis bacteriophora* and *Heterorhabditis megidis*, from The Pesticide Manual, 11$^{th}$Ed. (1997), The British Crop Protection Council, London, page 671; *Steinernema feltiae*, from The Pesticide Manual, 11$^{th}$Ed. (1997), The British Crop Protection Council, London, page 1115 and *Steinernema scapterisci*, from The Pesticide Manual, 11$^{th}$Ed. (1997), The British Crop Protection Council, London, page 1116;

(LIV) a preparation obtainable from *Bacillus subtilis*, from The Pesticide Manual, 11$^{th}$Ed. (1997), The British Crop Protection Council, London, page 72; or from a strain of *Bacillus thuringiensis* with the exception of compounds isolated from GC91 or from NCTC11821; The Pesticide Manual, 11$^{th}$Ed. (1997), The British Crop Protection Council, London, page 73;

(LV) a preparation which contains insect-active fungi, preferably *Verticillium lecanii*, from The Pesticide Manual, 11$^{th}$Ed. (1997), The British Crop Protection Council, London, page 1266; *Beauveria brogniartii*, from The Pesticide Manual, 11$^{th}$Ed. (1997), The British Crop Protection Council, London, page 85 and *Beauveria bassiana*, from The Pesticide Manual, 11$^{th}$Ed. (1997), The British Crop Protection Council, London, page 83;

(LVI) a preparation which contains insect-active viruses, preferably Neodipridon Sertifer NPV, from The Pesticide Manual, 11$^{th}$Ed. (1997), The British Crop Protection Council, London, page 1342; *Mamestra brassicae* NPV, from The Pesticide Manual, 11$^{th}$Ed. (1997), The British Crop Protection Council, London, page 759 and *Cydia pomonella granulosis* virus, from The Pesticide Manual, 11$^{th}$Ed. (1997), The British Crop Protection Council, London, page 291;

(CLXXXI) 7-Chloro-2,3,4a,5-tetrahydro-2-[methoxycarbonyl(4-trifluoromethoxyphenyl)carbamoyl]indole[1,2e]oxazolin-4a-carboxylate(DPX-MP062, Indoxycarb), from The Pesticide Manual, 11$^{th}$Ed. (1997), The British Crop Protection Council, London, page 453;

(CLXXXII) N'-tert.-butyl-N'-(3,5-dimethylbenzoyl)-3-methoxy-2-methylbenzohydrazide (RH-2485, Methoxyfenozide), from The Pesticide Manual, 11$^{th}$Ed. (1997), The British Crop Protection Council, London, page 1094; and (CLXXXIII) (N'-[4-methoxy-biphenyl-3-yl]-hydrazinecarboxylic acid isopropyl ester (D 2341), from Brighton Crop Protection Conference, 1996, 487–493;

(R2) Book of Abstracts, 212th ACS National Meeting Orlando, Fla., Aug. 25–29 (1996), AGRO-020. Publisher American Chemical Society, Washington, D.C. CONEN: 63BFAF.

As a consequence of the above details, a further essential aspect of the present invention relates to combination preparations for the control of parasites on warm-blooded animals, characterised in that they contain, in addition to a compound of formula I, at least one further active ingredient having the same or different sphere of activity and at least one physiologically acceptable carrier. The present invention is not restricted to two-fold combinations.

As a rule, the anthelminthic compositions according to the invention contain 0.1 to 99% by weight, especially 0.1 to 95% by weight of active ingredient of formula I, Ia or mixtures thereof, 99.9 to 1% by weight, especially 99.8 to 5% by weight of a solid or liquid admixture, including 0 to 25% by weight, especially 0.1 to 25% by weight of a surfactant.

The pour-on or spot-on method consists in applying the compound of formula I to a specific location of the skin or coat, advantageously to the neck or backbone of the animal. This takes place e.g. by applying a swab or spray of the pour-on or spot-on formulation to a relatively small area of the coat, from where the active substance is dispersed almost automatically over wide areas of the fur owing to the spreading nature of the components in the formulaton and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyidodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$–$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

A pour-on or spot-on formulation generally contains 1 to 20% by weight of a compound of formula I, 0.1 to 50% by weight of dispersing agent and 45 to 98.9% by weight of solvent.

The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

Whereas it is preferred to formulate commercial products as concentrates, the end user will normally use dilute formulations.

Such compositions may also contain further additives, such as stabilisers, anti-foaming agents, viscosity regulators, binding agents or tackifiers, as well as other active ingredients, in order to achieve special effects.

Anthelminthic compositions of this type, which are used by the end user, similarly form a constituent of the present invention.

In each of the processes according to the invention for pest control or in each of the pest control compositions according to the invention, the active ingredients of formula I can be used in all of their steric configurations or in mixtures thereof.

The invention also includes a method of prophylactically protecting warm-blooded animals, especially productive livestock, domestic animals and pets, against parasitic helminths, which is characterised in that the active ingredients of formula I or the active ingredient formulations prepared therefrom are administered to the animals as an additive to the feed, or to the drinks or also in solid or liquid form, orally or by injection or parenterally. The invention also includes the compounds of formula I according to the invention for usage in one of the said processes.

The following examples serve merely to illustrate the invention without restricting it, the term active ingredient representing a substance listed in table 1.

In particular, preferred formulations are made up as follows:

(%=percent by weight)

FORMULATION EXAMPLES

| 1. Emulsion concentrates | a) | b) | c) |
| --- | --- | --- | --- |
| active ingredient | 25% | 40% | 50% |
| Ca dodecylbenzene sulphonate | 5% | 8% | 6% |
| castor oil polyethylene glycol ether (36 mols ethylene oxide) | 5% | — | — |
| tributylphenolpolyethylene glycol ether (30 mols ethylene oxide) | — | 12% | 4% |
| cyclohexanone | — | 15% | 20% |
| xylene mixture | 65% | 25% | 20% |

From these concentrates, emulsions of any desired concentration may be prepared by diluting with water.

| 2. Emulsion concentrates | a) | b) | c) |
| --- | --- | --- | --- |
| active ingredient | 10% | 8% | 60% |
| octylphenol polyethylene glycol ether (4–5 mols ethylene oxide) | 3% | 3% | 2% |
| Ca dodecylbenzene sulphonate | 3% | 4% | 4% |
| castor oil polyethylene glycol ether (35 mols ethylene oxide) | 4% | 5% | 4% |
| cyclohexanone | 30% | 40% | 15% |
| xylene mixture | 50% | 40% | 15% |

From these concentrates, emulsions of any desired concentration may be prepared by diluting with water.

| 3. Suspension concentrate | |
| --- | --- |
| active ingredient | 40% |
| ethylene glycol | 10% |
| nonylphenol polyethylene glycol ether (15 mols ethylene oxide) | 6% |
| Na ligninsulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the admixtures. In this way, a suspension concentrate is obtained, from which suspensions of any desired concentration can be prepared by diluting with water.

| 4. Powder mixtures that are dispersible in water | a) | b) | c) |
| --- | --- | --- | --- |
| active ingredient | 25% | 50% | 75% |
| Na ligninsulphonate | 5% | 5% | — |
| oleic acid | 3% | — | 5% |
| Na diisobutylnaphthalene sulphonate | — | 6% | 10% |
| octylphenol polyethylene glycol ether (7–8 mols ethylene oxide) | — | 2% | — |
| highly dispersed silicic acid | 5% | 10% | 10% |
| kaolin | 62% | 27% | — |

The active ingredient is mixed thoroughly with the admixtures and ground well in an appropriate mill. Wettable powders are obtained, which may be diluted with water to form suspensions of any desired concentration.

| 5. Dusts | a) | b) |
| --- | --- | --- |
| active ingredient | 2% | 5% |
| highly dispersed silicic acid | 1% | 5% |
| talc | 97% | — |
| kaolin | — | 90% |

By intimately mixing the carriers with the active ingredient and grinding the mixture, ready-to-use dusts are obtained.

| 6. Granulate | a) | b) |
| --- | --- | --- |
| active ingredient | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent subsequently concentrated by evaporation under vacuum. Granulates of this kind can be mixed with the fodder.

| 7. Granulate | |
| --- | --- |
| active ingredient | 10% |
| Na ligninsulphonate | 2% |
| carboxymethylcellulose | 1% |
| kaolin | 87% |

The active ingredient is mixed with the admixtures, ground and moistened with water. This mixture is extruded and then dried in a stream of air.

| 8. Granulate | |
| --- | --- |
| active ingredient | 3% |
| polyethylene glycol (mw 200) | 3% |
| kaolin | 94% |

(mw = molecular weight)

The finely ground active ingredient is evenly applied in a mixer to the kaolin which has been moistened with polyethylene glycol. In this way, dust-free coated granules are obtained.

| 9. Tablets or boli | | |
|---|---|---|
| I | active ingredient | 33.00% |
| | methylcellulose | 0.80% |
| | silicic acid, highly dispersed | 0.80% |
| | corn starch | 8.40% |
| II | lactose, cryst. | 22.50% |
| | corn starch | 17.00% |
| | microcryst. cellulose | 16.50% |
| | magnesium stearate | 1.00% |

I Methyl cellulose is stirred into water. After the material has swollen, silicic acid is stirred in and the mixture homogeneously suspended. The active ingredient and the corn starch are mixed. The aqueous suspension is worked into this mixture and kneaded to a dough. The resulting mass is granulated through a 12 M sieve and dried.

II All 4 excipients are mixed thoroughly.

III The preliminary mixes obtained according to I and II are mixed and pressed into tablets or boli.

| 10. Injectables | | |
|---|---|---|
| A. Oily vehicle (slow release) | | |
| 1. | active ingredient | 0.1–1.0 g |
| | groundnut oil | ad 100 ml |
| 2. | active ingredient | 0.1–1.0 g |
| | sesame oil | ad 100 ml |

Preparation: The active ingredient is dissolved in part of the oil whilst stirring and, if required, with gentle heating, then after cooling made up to the desired volume and sterile-filtered through a suitable membrane filter with a pore size of 0.22 mm.

| B Water-miscible solvent (average rate of release) | |
|---|---|
| active ingredient | 0.1–1.0 g |
| 4-hydroxymethyl-1,3-dioxolane (glycerol formal) | 40 g |
| 1,2-propanediol | ad 100 ml |
| an active ingredient | 0.1–1.0 g |
| glycerol dimethyl ketal | 40 g |
| 1,2-propanediol | ad 100 ml |

Preparation: The active ingredient is dissolved in part of the solvent whilst stirring, made up to the desired volume and sterile-filtered through a suitable membrane filter with a pore size of 0.22 mm.

| C. Aqueous solubilisate (rapid release) | |
|---|---|
| 1. active ingredient | 0.1–1.0 g |
| polyethoxylated castor oil (40 ethylene oxide units) | 10 g |
| 1,2-propanediol | 20 g |
| benzyl alcohol | 1 g |
| Aqua ad inject. | ad 100 ml |
| 2. active ingredient | 0.1–1.0 g |
| polyethoxylated sorbitan monooleate (20 ethylene oxide units) | 8 g |
| 4-hydroxymethyl-1,3-dioxolane (glycerol formal) | 20 g |

| -continued | |
|---|---|
| C. Aqueous solubilisate (rapid release) | |
| benzyl alcohol | 1 g |
| Aqua ad inject. | ad 100 ml |

Preparation: The active ingredient is dissolved in the solvents and the surfactant, and made up with water to the desired volume. Sterile filtration through an appropriate membrane filter of 0.22 mm pore size.

| 11. Pour on | |
|---|---|
| A. | |
| active ingredient | 5 g |
| isopropyl myristate | 10 g |
| isopropanol | ad 100 ml |
| B | |
| active ingredient | 2 g |
| hexyl laurate | 5 g |
| medium-chained triglycerides | 15 g |
| ethanol | ad 100 ml |
| C. | |
| active ingredient | 2 g |
| oleyl oleate | 5 g |
| N-methyl-pyrrolidone | 40 g |
| isopropanol | ad 100 ml |

The aqueous systems may also preferably be used for oral and/or intraruminal application.

The compositions may also contain further additives, such as stabilisers, e.g. where appropriate epoxidised vegetable oils (epoxidised coconut oil, rapeseed oil, or soybean oil); antifoams, typically silicone oil, preservatives, viscosity regulators, binders, tackifiers, as well as fertilisers or other chemical agents to achieve special effects.

Further biologically active substances or additives, which are neutral towards the compounds of formula I and do not have a harmful effect on the host animal to be treated, as well as mineral salts or vitamins, may also be added to the described compositions.

The following examples serve to illustrate the invention. They do not limit the invention. The letter 'h' stands for hour.

PREPARATION EXAMPLE

N-(5-Cyano-4-trifluoromethylthiazol-2-yl)-2-(2,4-dichlorophenoxy)-1-methoximinobutyric Acid Amide 1 drop of dimethylformamide and 283 mg of oxalyl chloride are added to a solution of 500 mg of 2-(2,4-dichlorophenoxy)-1-methoximinobutyric acid in 10 ml of dichloromethane, and stirred first of all for 10 minutes at room temperature, and then for a further 10 minutes under reflux. The reaction mixture is subsequently concentrated under vacuum, diluted with 4 ml of dichloromethane, and added dropwise to a solution of 223 mg of triethylamine and 330 mg of 2-amino-5-cyano-4-trifluoromethylthiazole in 20 ml of tetrahydrofuran. After stirring for 12 hours at room temperature, the mixture is concentrated by evaporation under vacuum, and the residue chromatographed on a column of silica gel with hexane/ethyl acetate (5:1), whereby the product is obtained as a waxy compound.

The substances named in the following table may also be prepared analogously to the above-described method. The values of the melting points are given in ° C.

TABLE 1

| No. | X₁ | X₂ | R₁ | R₂ | R₅ | (R₉)m | phys. data |
|---|---|---|---|---|---|---|---|
| 1.1 | N | N | Cl | H | H | H | |
| 1.2 | N | N | Cl | H | H | 2-F | |
| 1.3 | N | N | Cl | H | H | 4-F | |
| 1.4 | N | N | Cl | H | H | 2,4-F₂ | |
| 1.5 | N | N | Cl | H | H | 2-Cl | |
| 1.6 | N | N | Cl | H | H | 4-Cl | |
| 1.7 | N | N | Cl | H | H | 2,4-Cl₂ | |
| 1.8 | N | N | Cl | H | H | 4-CF₃ | |
| 1.9 | N | N | Cl | H | H | 4-CN | |
| 1.10 | N | N | Cl | H | H | 4-phenoxy | |
| 1.11 | N | N | Cl | H | CH₃ | H | |
| 1.12 | N | N | Cl | H | CH₃ | 2-F | |
| 1.13 | N | N | Cl | H | CH₃ | 4-F | |
| 1.14 | N | N | Cl | H | CH₃ | 2,4-F₂ | |
| 1.15 | N | N | Cl | H | CH₃ | 2-Cl | |
| 1.16 | N | N | Cl | H | CH₃ | 4-Cl | |
| 1.17 | N | N | Cl | H | CH₃ | 2,4-Cl₂ | |
| 1.18 | N | N | Cl | H | CH₃ | 4-CF₃ | |
| 1.19 | N | N | Cl | H | CH₃ | 4-CN | |
| 1.20 | N | N | Cl | H | CH₃ | 4-phenoxy | |
| 1.21 | N | N | Cl | CH₃ | H | H | |
| 1.22 | N | N | Cl | CH₃ | H | 2-F | |
| 1.23 | N | N | Cl | CH₃ | H | 4-F | |
| 1.24 | N | N | Cl | CH₃ | H | 2,4-F₂ | |
| 1.25 | N | N | Cl | CH₃ | H | 2-Cl | |
| 1.26 | N | N | Cl | CH₃ | H | 4-Cl | |
| 1.27 | N | N | Cl | CH₃ | H | 2,4-Cl₂ | |
| 1.28 | N | N | Cl | CH₃ | H | 4-CF₃ | |
| 1.29 | N | N | Cl | CH₃ | H | 4-CN | |
| 1.30 | N | N | Cl | CH₃ | H | 4-phenoxy | |
| 1.31 | N | N | Cl | CH₃ | CH₃ | H | |
| 1.32 | N | N | Cl | CH₃ | CH₃ | 2-F | |
| 1.33 | N | N | Cl | CH₃ | CH₃ | 4-F | |
| 1.34 | N | N | Cl | CH₃ | CH₃ | 2,4-F₂ | |
| 1.35 | N | N | Cl | CH₃ | CH₃ | 2-Cl | |
| 1.36 | N | N | Cl | CH₃ | CH₃ | 4-Cl | |
| 1.37 | N | N | Cl | CH₃ | CH₃ | 2,4-Cl₂ | |
| 1.38 | N | N | Cl | CH₃ | CH₃ | 4-CF₃ | |
| 1.39 | N | N | Cl | CH₃ | CH₃ | 4-CN | |
| 1.40 | N | N | Cl | CH₃ | CH₃ | 4-phenoxy | |
| 1.41 | N | N | CF₃ | H | H | H | |
| 1.42 | N | N | CF₃ | H | H | 2-F | |
| 1.43 | N | N | CF₃ | H | H | 4-F | |
| 1.44 | N | N | CF₃ | H | H | 2,4-F₂ | |
| 1.45 | N | N | CF₃ | H | H | 2-Cl | |
| 1.46 | N | N | CF₃ | H | H | 4-Cl | |
| 1.47 | N | N | CF₃ | H | H | 2,4-Cl₂ | |
| 1.48 | N | N | CF₃ | H | H | 4-CF₃ | |
| 1.49 | N | N | CF₃ | H | H | 4-CN | |
| 1.50 | N | N | CF₃ | H | H | 4-phenoxy | |
| 1.51 | N | N | CF₃ | H | CH₃ | H | |
| 1.52 | N | N | CF₃ | H | CH₃ | 2-F | |
| 1.53 | N | N | CF₃ | H | CH₃ | 4-F | |
| 1.54 | N | N | CF₃ | H | CH₃ | 2,4-F₂ | |
| 1.55 | N | N | CF₃ | H | CH₃ | 2-Cl | |
| 1.56 | N | N | CF₃ | H | CH₃ | 4-Cl | |
| 1.57 | N | N | CF₃ | H | CH₃ | 2,4-Cl₂ | |
| 1.58 | N | N | CF₃ | H | CH₃ | 4-CF₃ | |
| 1.59 | N | N | CF₃ | H | CH₃ | 4-CN | |
| 1.60 | N | N | CF₃ | H | CH₃ | 4-phenoxy | |
| 1.61 | N | N | CF₃ | CH₃ | H | H | |
| 1.62 | N | N | CF₃ | CH₃ | H | 2-F | |
| 1.63 | N | N | CF₃ | CH₃ | H | 4-F | |
| 1.64 | N | N | CF₃ | CH₃ | H | 2,4-F₂ | |
| 1.65 | N | N | CF₃ | CH₃ | H | 2-Cl | |
| 1.66 | N | N | CF₃ | CH₃ | H | 4-Cl | |
| 1.67 | N | N | CF₃ | CH₃ | H | 2,4-Cl₂ | |
| 1.68 | N | N | CF₃ | CH₃ | H | 4-CF₃ | |
| 1.69 | N | N | CF₃ | CH₃ | H | 4-CN | |
| 1.70 | N | N | CF₃ | CH₃ | H | 4-phenoxy | |
| 1.71 | N | N | CF₃ | CH₃ | CH₃ | H | |
| 1.72 | N | N | CF₃ | CH₃ | CH₃ | 2-F | |
| 1.73 | N | N | CF₃ | CH₃ | CH₃ | 4-F | |
| 1.74 | N | N | CF₃ | CH₃ | CH₃ | 2,4-F₂ | |
| 1.75 | N | N | CF₃ | CH₃ | CH₃ | 2-Cl | |
| 1.76 | N | N | CF₃ | CH₃ | CH₃ | 4-Cl | |
| 1.77 | N | N | CF₃ | CH₃ | CH₃ | 2,4-Cl₂ | |
| 1.78 | N | N | CF₃ | CH₃ | CH₃ | 4-CF₃ | |
| 1.79 | N | N | CF₃ | CH₃ | CH₃ | 4-CN | |
| 1.80 | N | N | CF₃ | CH₃ | CH₃ | 4-phenoxy | |
| 1.81 | N | C(CN) | Cl | H | H | H | |
| 1.82 | N | C(CN) | Cl | H | H | 2-F | |
| 1.83 | N | C(CN) | Cl | H | H | 4-F | |
| 1.84 | N | C(CN) | Cl | H | H | 2,4-F₂ | |
| 1.85 | N | C(CN) | Cl | H | H | 2-Cl | |
| 1.86 | N | C(CN) | Cl | H | H | 4-Cl | |
| 1.87 | N | C(CN) | Cl | H | H | 2,4-Cl₂ | |
| 1.88 | N | C(CN) | Cl | H | H | 4-CF₃ | |
| 1.89 | N | C(CN) | Cl | H | H | 4-CN | |
| 1.90 | N | C(CN) | Cl | H | H | 4-phenoxy | |
| 1.91 | N | C(CN) | Cl | H | CH₃ | H | |
| 1.92 | N | C(CN) | Cl | H | CH₃ | 2-F | |
| 1.93 | N | C(CN) | Cl | H | CH₃ | 4-F | |
| 1.94 | N | C(CN) | Cl | H | CH₃ | 2,4-F₂ | |
| 1.95 | N | C(CN) | Cl | H | CH₃ | 2-Cl | |
| 1.96 | N | C(CN) | Cl | H | CH₃ | 4-Cl | |
| 1.97 | N | C(CN) | Cl | H | CH₃ | 2,4-Cl₂ | |
| 1.98 | N | C(CN) | Cl | H | CH₃ | 4-CF₃ | |
| 1.99 | N | C(CN) | Cl | H | CH₃ | 4-CN | |
| 1.100 | N | C(CN) | Cl | H | CH₃ | 4-phenoxy | |
| 1.101 | N | C(CN) | Cl | CH₃ | H | H | |
| 1.102 | N | C(CN) | Cl | CH₃ | H | 2-F | |
| 1.103 | N | C(CN) | Cl | CH₃ | H | 4-F | |
| 1.104 | N | C(CN) | Cl | CH₃ | H | 2,4-F₂ | |
| 1.105 | N | C(CN) | Cl | CH₃ | H | 2-Cl | |
| 1.106 | N | C(CN) | Cl | CH₃ | H | 4-Cl | |
| 1.107 | N | C(CN) | Cl | CH₃ | H | 2,4-Cl₂ | |
| 1.108 | N | C(CN) | Cl | CH₃ | H | 4-CF₃ | |
| 1.109 | N | C(CN) | Cl | CH₃ | H | 4-CN | |
| 1.110 | N | C(CN) | Cl | CH₃ | H | 4-phenoxy | |
| 1.111 | N | C(CN) | Cl | CH₃ | CH₃ | H | |
| 1.112 | N | C(CN) | Cl | CH₃ | CH₃ | 2-F | |
| 1.113 | N | C(CN) | Cl | CH₃ | CH₃ | 4-F | |
| 1.114 | N | C(CN) | Cl | CH₃ | CH₃ | 2,4-F₂ | |
| 1.115 | N | C(CN) | Cl | CH₃ | CH₃ | 2-Cl | |
| 1.116 | N | C(CN) | Cl | CH₃ | CH₃ | 4-Cl | |
| 1.117 | N | C(CN) | Cl | CH₃ | CH₃ | 2,4-Cl₂ | |
| 1.118 | N | C(CN) | Cl | CH₃ | CH₃ | 4-CF₃ | |
| 1.119 | N | C(CN) | Cl | CH₃ | CH₃ | 4-CN | |
| 1.120 | N | C(CN) | Cl | CH₃ | CH₃ | 4-phenoxy | |
| 1.121 | N | C(CN) | CF₃ | H | H | H | |
| 1.122 | N | C(CN) | CF₃ | H | H | 2-F | |
| 1.123 | N | C(CN) | CF₃ | H | H | 4-F | |
| 1.124 | N | C(CN) | CF₃ | H | H | 2,4-F₂ | |
| 1.125 | N | C(CN) | CF₃ | H | H | 2-Cl | |
| 1.126 | N | C(CN) | CF₃ | H | H | 4-Cl | |
| 1.127 | N | C(CN) | CF₃ | H | H | 2,4-Cl₂ | |
| 1.128 | N | C(CN) | CF₃ | H | H | 4-CF₃ | |
| 1.129 | N | C(CN) | CF₃ | H | H | 4-CN | |
| 1.130 | N | C(CN) | CF₃ | H | H | 4-phenoxy | |
| 1.131 | N | C(CN) | CF₃ | H | CH₃ | H | |
| 1.132 | N | C(CN) | CF₃ | H | CH₃ | 2-F | |

TABLE 1-continued

| No. | $X_1$ | $X_2$ | $R_1$ | $R_2$ | $R_5$ | $(R_9)m$ | phys. data |
|---|---|---|---|---|---|---|---|
| 1.133 | N | C(CN) | $CF_3$ | H | $CH_3$ | 4-F | |
| 1.134 | N | C(CN) | $CF_3$ | H | $CH_3$ | 2,4-$F_2$ | |
| 1.135 | N | C(CN) | $CF_3$ | H | $CH_3$ | 2-Cl | |
| 1.136 | N | C(CN) | $CF_3$ | H | $CH_3$ | 4-Cl | |
| 1.137 | N | C(CN) | $CF_3$ | H | $CH_3$ | 2,4-$Cl_2$ | waxy |
| 1.138 | N | C(CN) | $CF_3$ | H | $CH_3$ | 4-$CF_3$ | |
| 1.139 | N | C(CN) | $CF_3$ | H | $CH_3$ | 4-CN | |
| 1.140 | N | C(CN) | $CF_3$ | H | $CH_3$ | 4-phenoxy | |
| 1.141 | N | C(CN) | $CF_3$ | $CH_3$ | H | H | |
| 1.142 | N | C(CN) | $CF_3$ | $CH_3$ | H | 2-F | |
| 1.143 | N | C(CN) | $CF_3$ | $CH_3$ | H | 4-F | |
| 1.144 | N | C(CN) | $CF_3$ | $CH_3$ | H | 2,4-$F_2$ | |
| 1.145 | N | C(CN) | $CF_3$ | $CH_3$ | H | 2-Cl | |
| 1.146 | N | C(CN) | $CF_3$ | $CH_3$ | H | 4-Cl | |
| 1.147 | N | C(CN) | $CF_3$ | $CH_3$ | H | 2,4-$Cl_2$ | |
| 1.148 | N | C(CN) | $CF_3$ | $CH_3$ | H | 4-$CF_3$ | |
| 1.149 | N | C(CN) | $CF_3$ | $CH_3$ | H | 4-CN | |
| 1.150 | N | C(CN) | $CF_3$ | $CH_3$ | H | 4-phenoxy | |
| 1.151 | N | C(CN) | $CF_3$ | $CH_3$ | $CH_3$ | H | |
| 1.152 | N | C(CN) | $CF_3$ | $CH_3$ | $CH_3$ | 2-F | |
| 1.153 | N | C(CN) | $CF_3$ | $CH_3$ | $CH_3$ | 4-F | |
| 1.154 | N | C(CN) | $CF_3$ | $CH_3$ | $CH_3$ | 2,4-$F_2$ | |
| 1.155 | N | C(CN) | $CF_3$ | $CH_3$ | $CH_3$ | 2-Cl | |
| 1.156 | N | C(CN) | $CF_3$ | $CH_3$ | $CH_3$ | 4-Cl | |
| 1.157 | N | C(CN) | $CF_3$ | $CH_3$ | $CH_3$ | 2,4-$Cl_2$ | |
| 1.158 | N | C(CN) | $CF_3$ | $CH_3$ | $CH_3$ | 4-$CF_3$ | |
| 1.159 | N | C(CN) | $CF_3$ | $CH_3$ | $CH_3$ | 4-CN | |
| 1.160 | N | C(CN) | $CF_3$ | $CH_3$ | $CH_3$ | 4-phenoxy | |
| 1.161 | C(CN) | N | Cl | H | H | H | |
| 1.162 | C(CN) | N | Cl | H | H | 2-F | |
| 1.163 | C(CN) | N | Cl | H | H | 4-F | |
| 1.164 | C(CN) | N | Cl | H | H | 2,4-$F_2$ | |
| 1.165 | C(CN) | N | Cl | H | H | 2-Cl | |
| 1.166 | C(CN) | N | Cl | H | H | 4-Cl | |
| 1.167 | C(CN) | N | Cl | H | H | 2,4-$Cl_2$ | |
| 1.168 | C(CN) | N | Cl | H | H | 4-$CF_3$ | |
| 1.169 | C(CN) | N | Cl | H | H | 4-CN | |
| 1.170 | C(CN) | N | Cl | H | H | 4-phenoxy | |
| 1.171 | C(CN) | N | Cl | H | $CH_3$ | H | |
| 1.172 | C(CN) | N | Cl | H | $CH_3$ | 2-F | |
| 1.173 | C(CN) | N | Cl | H | $CH_3$ | 4-F | |
| 1.174 | C(CN) | N | Cl | H | $CH_3$ | 2,4-$F_2$ | |
| 1.175 | C(CN) | N | Cl | H | $CH_3$ | 2-Cl | |
| 1.176 | C(CN) | N | Cl | H | $CH_3$ | 4-Cl | |
| 1.177 | C(CN) | N | Cl | H | $CH_3$ | 2,4-$Cl_2$ | 140–141° C. |
| 1.178 | C(CN) | N | Cl | H | $CH_3$ | 4-$CF_3$ | |
| 1.179 | C(CN) | N | Cl | H | $CH_3$ | 4-CN | |
| 1.180 | C(CN) | N | Cl | H | $CH_3$ | 4-phenoxy | |
| 1.181 | C(CN) | N | Cl | $CH_3$ | H | H | |
| 1.182 | C(CN) | N | Cl | $CH_3$ | H | 2-F | |
| 1.183 | C(CN) | N | Cl | $CH_3$ | H | 4-F | |
| 1.184 | C(CN) | N | Cl | $CH_3$ | H | 2,4-$F_2$ | |
| 1.185 | C(CN) | N | Cl | $CH_3$ | H | 2-Cl | |
| 1.186 | C(CN) | N | Cl | $CH_3$ | H | 4-Cl | |
| 1.187 | C(CN) | N | Cl | $CH_3$ | H | 2,4-$Cl_2$ | |
| 1.188 | C(CN) | N | Cl | $CH_3$ | H | 4-$CF_3$ | |
| 1.189 | C(CN) | N | Cl | $CH_3$ | H | 4-CN | |
| 1.190 | C(CN) | N | Cl | $CH_3$ | H | 4-phenoxy | |
| 1.191 | C(CN) | N | Cl | $CH_3$ | $CH_3$ | H | |
| 1.192 | C(CN) | N | Cl | $CH_3$ | $CH_3$ | 2-F | |
| 1.193 | C(CN) | N | Cl | $CH_3$ | $CH_3$ | 4-F | |
| 1.194 | C(CN) | N | Cl | $CH_3$ | $CH_3$ | 2,4-$F_2$ | |
| 1.195 | C(CN) | N | Cl | $CH_3$ | $CH_3$ | 2-Cl | |
| 1.196 | C(CN) | N | Cl | $CH_3$ | $CH_3$ | 4-Cl | |
| 1.197 | C(CN) | N | Cl | $CH_3$ | $CH_3$ | 2,4-$Cl_2$ | |
| 1.198 | C(CN) | N | Cl | $CH_3$ | $CH_3$ | 4-$CF_3$ | |
| 1.199 | C(CN) | N | Cl | $CH_3$ | $CH_3$ | 4-CN | |
| 1.200 | C(CN) | N | Cl | $CH_3$ | $CH_3$ | 4-phenoxy | |
| 1.201 | C(CN) | N | $CF_3$ | H | H | H | |
| 1.202 | C(CN) | N | $CF_3$ | H | H | 2-F | |
| 1.203 | C(CN) | N | $CF_3$ | H | H | 4-F | |
| 1.204 | C(CN) | N | $CF_3$ | H | H | 2,4-$F_2$ | |
| 1.205 | C(CN) | N | $CF_3$ | H | H | 2-Cl | |
| 1.206 | C(CN) | N | $CF_3$ | H | H | 4-Cl | |
| 1.207 | C(CN) | N | $CF_3$ | H | H | 2,4-$Cl_2$ | |
| 1.208 | C(CN) | N | $CF_3$ | H | H | 4-$CF_3$ | |
| 1.209 | C(CN) | N | $CF_3$ | H | H | 4-CN | |
| 1.210 | C(CN) | N | $CF_3$ | H | H | 4-phenoxy | |
| 1.211 | C(CN) | N | $CF_3$ | H | $CH_3$ | H | |
| 1.212 | C(CN) | N | $CF_3$ | H | $CH_3$ | 2-F | |
| 1.213 | C(CN) | N | $CF_3$ | H | $CH_3$ | 4-F | |
| 1.214 | C(CN) | N | $CF_3$ | H | $CH_3$ | 2,4-$F_2$ | |
| 1.215 | C(CN) | N | $CF_3$ | H | $CH_3$ | 2-Cl | |
| 1.216 | C(CN) | N | $CF_3$ | H | $CH_3$ | 4-Cl | |
| 1.217 | C(CN) | N | $CF_3$ | H | $CH_3$ | 2,4-$Cl_2$ | |
| 1.218 | C(CN) | N | $CF_3$ | H | $CH_3$ | 4-$CF_3$ | |
| 1.219 | C(CN) | N | $CF_3$ | H | $CH_3$ | 4-CN | |
| 1.220 | C(CN) | N | $CF_3$ | H | $CH_3$ | 4-phenoxy | |
| 1.221 | C(CN) | N | $CF_3$ | $CH_3$ | H | H | |
| 1.222 | C(CN) | N | $CF_3$ | $CH_3$ | H | 2-F | |
| 1.223 | C(CN) | N | $CF_3$ | $CH_3$ | H | 4-F | |
| 1.224 | C(CN) | N | $CF_3$ | $CH_3$ | H | 2,4-$F_2$ | |
| 1.225 | C(CN) | N | $CF_3$ | $CH_3$ | H | 2-Cl | |
| 1.226 | C(CN) | N | $CF_3$ | $CH_3$ | H | 4-Cl | |
| 1.227 | C(CN) | N | $CF_3$ | $CH_3$ | H | 2,4-$Cl_2$ | |
| 1.228 | C(CN) | N | $CF_3$ | $CH_3$ | H | 4-$CF_3$ | |
| 1.229 | C(CN) | N | $CF_3$ | $CH_3$ | H | 4-CN | |
| 1.230 | C(CN) | N | $CF_3$ | $CH_3$ | H | 4-phenoxy | |
| 1.231 | C(CN) | N | $CF_3$ | $CH_3$ | $CH_3$ | H | |
| 1.232 | C(CN) | N | $CF_3$ | $CH_3$ | $CH_3$ | 2-F | |
| 1.233 | C(CN) | N | $CF_3$ | $CH_3$ | $CH_3$ | 4-F | |
| 1.234 | C(CN) | N | $CF_3$ | $CH_3$ | $CH_3$ | 2,4-$F_2$ | |
| 1.235 | C(CN) | N | $CF_3$ | $CH_3$ | $CH_3$ | 2-Cl | |
| 1.236 | C(CN) | N | $CF_3$ | $CH_3$ | $CH_3$ | 4-Cl | |
| 1.237 | C(CN) | N | $CF_3$ | $CH_3$ | $CH_3$ | 2,4-$Cl_2$ | |
| 1.238 | C(CN) | N | $CF_3$ | $CH_3$ | $CH_3$ | 4-$CF_3$ | |
| 1.239 | C(CN) | N | $CF_3$ | $CH_3$ | $CH_3$ | 4-CN | |
| 1.240 | C(CN) | N | $CF_3$ | $CH_3$ | $CH_3$ | 4-phenoxy | |
| 1.241 | C(CN) | C(CN) | Cl | H | H | H | |
| 1.242 | C(CN) | C(CN) | Cl | H | H | 2-F | |
| 1.243 | C(CN) | C(CN) | Cl | H | H | 4-F | |
| 1.244 | C(CN) | C(CN) | Cl | H | H | 2,4-$F_2$ | |
| 1.245 | C(CN) | C(CN) | Cl | H | H | 2-Cl | |
| 1.246 | C(CN) | C(CN) | Cl | H | H | 4-Cl | |
| 1.247 | C(CN) | C(CN) | Cl | H | H | 2,4-$Cl_2$ | |
| 1.248 | C(CN) | C(CN) | Cl | H | H | 4-$CF_3$ | |
| 1.249 | C(CN) | C(CN) | Cl | H | H | 4-CN | |
| 1.250 | C(CN) | C(CN) | Cl | H | H | 4-phenoxy | |
| 1.251 | C(CN) | C(CN) | Cl | H | $CH_3$ | H | |
| 1.252 | C(CN) | C(CN) | Cl | H | $CH_3$ | 2-F | |
| 1.253 | C(CN) | C(CN) | Cl | H | $CH_3$ | 4-F | |
| 1.254 | C(CN) | C(CN) | Cl | H | $CH_3$ | 2,4-$F_2$ | |
| 1.255 | C(CN) | C(CN) | Cl | H | $CH_3$ | 2-Cl | |
| 1.256 | C(CN) | C(CN) | Cl | H | $CH_3$ | 4-Cl | |
| 1.257 | C(CN) | C(CN) | Cl | H | $CH_3$ | 2,4-$Cl_2$ | |
| 1.258 | C(CN) | C(CN) | Cl | H | $CH_3$ | 4-$CF_3$ | |
| 1.259 | C(CN) | C(CN) | Cl | H | $CH_3$ | 4-CN | |
| 1.260 | C(CN) | C(CN) | Cl | H | $CH_3$ | 4-phenoxy | |
| 1.261 | C(CN) | C(CN) | Cl | $CH_3$ | H | H | |
| 1.262 | C(CN) | C(CN) | Cl | $CH_3$ | H | 2-F | |
| 1.263 | C(CN) | C(CN) | Cl | $CH_3$ | H | 4-F | |
| 1.264 | C(CN) | C(CN) | Cl | $CH_3$ | H | 2,4-$F_2$ | |
| 1.265 | C(CN) | C(CN) | Cl | $CH_3$ | H | 2-Cl | |
| 1.266 | C(CN) | C(CN) | Cl | $CH_3$ | H | 4-Cl | |
| 1.267 | C(CN) | C(CN) | Cl | $CH_3$ | H | 2,4-$Cl_2$ | |
| 1.268 | C(CN) | C(CN) | Cl | $CH_3$ | H | 4-$CF_3$ | |

TABLE 1-continued

[Structure: R₁-X₁-X₂-S ring connected to N(R₂)-C(=O)-CH(R₅)-O-phenyl-(R₉)ₘ with N-OCH₃ group]

| No. | X₁ | X₂ | R₁ | R₂ | R₅ | (R₉)ₘ | phys. data |
|---|---|---|---|---|---|---|---|
| 1.269 | C(CN) | C(CN) | Cl | CH₃ | H | 4-CN | |
| 1.270 | C(CN) | C(CN) | Cl | CH₃ | H | 4-phenoxy | |
| 1.271 | C(CN) | C(CN) | Cl | CH₃ | CH₃ | H | |
| 1.272 | C(CN) | C(CN) | Cl | CH₃ | CH₃ | 2-F | |
| 1.273 | C(CN) | C(CN) | Cl | CH₃ | CH₃ | 4-F | |
| 1.274 | C(CN) | C(CN) | Cl | CH₃ | CH₃ | 2,4-F₂ | |
| 1.275 | C(CN) | C(CN) | Cl | CH₃ | CH₃ | 2-Cl | |
| 1.276 | C(CN) | C(CN) | Cl | CH₃ | CH₃ | 4-Cl | |
| 1.277 | C(CN) | C(CN) | Cl | CH₃ | CH₃ | 2,4-Cl₂ | |
| 1.278 | C(CN) | C(CN) | Cl | CH₃ | CH₃ | 4-CF₃ | |
| 1.279 | C(CN) | C(CN) | Cl | CH₃ | CH₃ | 4-CN | |
| 1.280 | C(CN) | C(CN) | Cl | CH₃ | CH₃ | 4-phenoxy | |
| 1.281 | C(CN) | C(CN) | CF₃ | H | H | H | |
| 1.282 | C(CN) | C(CN) | CF₃ | H | H | 2-F | |
| 1.283 | C(CN) | C(CN) | CF₃ | H | H | 4-F | |
| 1.284 | C(CN) | C(CN) | CF₃ | H | H | 2,4-F₂ | |
| 1.285 | C(CN) | C(CN) | CF₃ | H | H | 2-Cl | |
| 1.286 | C(CN) | C(CN) | CF₃ | H | H | 4-Cl | |
| 1.287 | C(CN) | C(CN) | CF₃ | H | H | 2,4-Cl₂ | |
| 1.288 | C(CN) | C(CN) | CF₃ | H | H | 4-CF₃ | |
| 1.289 | C(CN) | C(CN) | CF₃ | H | H | 4-CN | |
| 1.290 | C(CN) | C(CN) | CF₃ | H | H | 4-phenoxy | |
| 1.291 | C(CN) | C(CN) | CF₃ | H | CH₃ | H | |
| 1.292 | C(CN) | C(CN) | CF₃ | H | CH₃ | 2-F | |
| 1.293 | C(CN) | C(CN) | CF₃ | H | CH₃ | 4-F | |
| 1.294 | C(CN) | C(CN) | CF₃ | H | CH₃ | 2,4-F₂ | |
| 1.295 | C(CN) | C(CN) | CF₃ | H | CH₃ | 2-Cl | |
| 1.296 | C(CN) | C(CN) | CF₃ | H | CH₃ | 4-Cl | |
| 1.297 | C(CN) | C(CN) | CF₃ | H | CH₃ | 2,4-Cl₂ | |
| 1.298 | C(CN) | C(CN) | CF₃ | H | CH₃ | 4-CF₃ | |
| 1.299 | C(CN) | C(CN) | CF₃ | H | CH₃ | 4-CN | |
| 1.300 | C(CN) | C(CN) | CF₃ | H | CH₃ | 4-phenoxy | |
| 1.301 | C(CN) | C(CN) | CF₃ | CH₃ | H | H | |
| 1.302 | C(CN) | C(CN) | CF₃ | CH₃ | H | 2-F | |
| 1.303 | C(CN) | C(CN) | CF₃ | CH₃ | H | 4-F | |
| 1.304 | C(CN) | C(CN) | CF₃ | CH₃ | H | 2,4-F₂ | |
| 1.305 | C(CN) | C(CN) | CF₃ | CH₃ | H | 2-Cl | |
| 1.306 | C(CN) | C(CN) | CF₃ | CH₃ | H | 4-Cl | |
| 1.307 | C(CN) | C(CN) | CF₃ | CH₃ | H | 2,4-Cl₂ | |
| 1.308 | C(CN) | C(CN) | CF₃ | CH₃ | H | 4-CF₃ | |
| 1.309 | C(CN) | C(CN) | CF₃ | CH₃ | H | 4-CN | |
| 1.310 | C(CN) | C(CN) | CF₃ | CH₃ | H | 4-phenoxy | |
| 1.311 | C(CN) | C(CN) | CF₃ | CH₃ | CH₃ | H | |
| 1.312 | C(CN) | C(CN) | CF₃ | CH₃ | CH₃ | 2-F | |
| 1.313 | C(CN) | C(CN) | CF₃ | CH₃ | CH₃ | 4-F | |
| 1.314 | C(CN) | C(CN) | CF₃ | CH₃ | CH₃ | 2,4-F₂ | |
| 1.315 | C(CN) | C(CN) | CF₃ | CH₃ | CH₃ | 2-Cl | |
| 1.316 | C(CN) | C(CN) | CF₃ | CH₃ | CH₃ | 4-Cl | |
| 1.317 | C(CN) | C(CN) | CF₃ | CH₃ | CH₃ | 2,4-Cl₂ | |
| 1.318 | C(CN) | C(CN) | CF₃ | CH₃ | CH₃ | 4-CF₃ | |
| 1.319 | C(CN) | C(CN) | CF₃ | CH₃ | CH₃ | 4-CN | |
| 1.320 | C(CN) | C(CN) | CF₃ | CH₃ | CH₃ | 4-phenoxy | |

BIOLOGICAL EXAMPLES

1. In-vivo test on *Trichostrongylus colubriformis* and *Haemonchus contortus* on Mongolian gerbils (*Meriones unquiculatus*) Using Subcutaneous Injection Six to eight week old Mongolian gerbils are infected by artificial feeding with ca. 2000 third instar larvae each of *T. colubriformis* and *H. contortus*. 6 days after infection, the gerbils are lightly anaesthetised with N₂O and treated by subcutaneous injection into the neck area with the test compounds, dissolved in a mixture of 2 parts DMSO and 1 part polyethylene glycol 400, in quantities of 100, 32 and 10–0.1 mg/kg. On day 9 (3 days after treatment), when most of the *H. contortus* that are still present are 4th instar larvae and most of the *T. colubriformis* are immature adults, the gerbils are killed in order to count the worms. The efficacy is calculated as the % reduction of the number of worms in each gerbil, compared with the geometric average of number of worms from 8 infected and untreated gerbils.

In this test, a vast reduction in nematode infestation is achieved with compounds of formula I.

Totally analogous results are obtained upon oral administration of the active ingredient.

2. Insecticidal Stomach Toxicant Activity on *Spodoptera littoralis*

Potted cotton plants at the 5-leaf stage are each sprayed with an acetonic/aqueous test solution containing 1, 3, 12.5 or 50 ppm of the compound to be tested.

After drying of the spray deposit, the plants are colonised with ca. 30 larvae ($L_1$ stage) of *Spodoptera littoralis*. Two plants are used per test compound and per test species. The test is carried out at ca. 24° C. and at 60% relative humidity. Evaluations and intermediate evaluations on moribund animals, larvae and feeding damage are made after 24, 48 and 72 h.

The compounds of formula I achieve total mortality after 24 h at a concentration of active ingredient of only 3 ppm.

3. Activity on Phytotoxic Acarids

OP-sensitive *Tetranychus urticae*

The primary leaves of bean plants (*Phaseolus vulgaris*) are covered 16 hours before the test with a mass-cultivated piece of leaf infested with *T. urticae*. After removing the piece of leaf, the plants that are infested with all stages of the mites are sprayed to drip point with a test solution containing either 0.2, 0.4 or 1.6 ppm of the compound to be tested. The temperature in the greenhouse is ca. 25° C. After 7 days, an evaluation of the percentage of mobile stages (adults and nymphs) and of eggs is made under a microscope.

The compounds of formula I achieve total mortality at a concentration of active ingredient of 0.4 ppm.

4. Activity on $L_1$ Larvae of *Lucilia sericata*

1 ml of an aqueous suspension of the active substance to be tested is admixed with 3 ml of a special larvae growth medium at ca. 50° C., so that a homogenate of either 250 or 125 ppm of active ingredient content is obtained. Ca. 30 *Lucilia* larvae ($L_1$) are used in each test tube sample. After 4 days, the mortality rate is determined. The compounds of formula I attain 100% activity with 250 ppm.

5. Acaricidal Activity on *Boophilus microplus* (Biarra Strain)

A piece of sticky tape is attached horizontally to a PVC sheet, so that 10 fully engorged female ticks of *Boophilus microplus* (Biarra strain) can be adhered thereto by their backs, side by side, in a row. Using an injection needle, 1 μl of a liquid is injected into each tick. The liquid is a 1:1 mixture of polyethylene glycol and acetone and it contains, dissolved therein, a certain amount of active ingredient chosen from 1, 0.1 or 0.01 μg per tick. Control animals are given an injection without active ingredient. After treatment, the animals are kept under normal conditions in an insectarium at ca. 28° C. and at 80% relative humidity until oviposition takes place and the larvae have hatched from the eggs of the control animals. The activity of a tested substance is determined by $IR_{90}$, i.e. an evaluation is made of the dosage of active ingredient at which 9 out of 10 female ticks (=90%) lay eggs that are infertile even after 30 days.

The compounds of formula I attain an $IR_{90}$ of 0.1 μg.

6. In vitro Efficacy on Engorged Female *Boophilus microolus* (BIARRA):

4×10 engorged female ticks of the OP-resistant BIARRA strain are adhered to a sticky strip and covered for 1 hour with a cotton wool ball soaked in an emulsion or suspension of the test compound in concentrations of 500, 125, 31 and 8 ppm respectively. Evaluation takes place 28 days later based on mortality, oviposition and hatched larvae.

An indication of the activity of the test compounds is shown by the number of females that

- die quickly before laying eggs,
- survive for some time without laying eggs,
- lay eggs in which no embryos are formed,
- lay eggs in which embryos form, from which no larvae hatch, and
- lay eggs in which embryos form, from which larvae normally hatch within 26 to 27 days.

In this test, the compounds of formula I effect more than 80% rapid mortality of the female ticks.

7. Contact Action on *Aphis craccivora*

Pea seedlings that have been infested with all stages of development of the aphids are sprayed with a solution of active ingredient prepared from an emulsion concentrate, the solution containing 50, 25 or 12.5 ppm of active ingredient, as desired. After 3 days, an evaluation is made of more than 80% of aphids that are either dead or have fallen off. Only at this level of activity is a preparation classified a s effective.

The compounds of formula I achieve total mortality (=100%) at a concentration of 12.5 ppm.

8. Larvicidal Aactivity on *Aedes aegypti*

A sufficient quantity of a 0.1% acetonic solution of the active ingredient for a chosen concentration of 10, 3.3 or 1.6 ppm to be attained, is added by pipette to the surface of 150 ml of water in a container. After evaporation of the acetone, the container is covered with ca. 30–40 3-day old Aedes larvae. After 1, 2 and 5 days, the mortality is tested.

In this test, the compounds of formula I at a concentration of 1.6 ppm effect complete mortality of all larvae after only one day.

9. In vivo Efficacy on Adult *Ctenocephalides felis* on Domestic Cats After Oral Treatment The test substances are given orally to domestic cats in a gelatin capsule before or after feeding, the dose varying between 0.5 and 20 mg/kg. On days 1, 3, 7 and 10 after treatment, each cat is exposed to 100 fleas (ca. 50 male and ca. 50 female), depending on the result of previous flea colonisation. The efficacy (in % reduction in flea numbers) is based on the number of living fleas found after combing for 10 minutes one day after each new flea colonisation, whereby the efficacy in % corresponds to the arithmetic average of the number of living fleas on control animals minus the number of living fleas on the treated animals, divided by the arithmetic average of the number of living fleas on control animals and multiplied by 100.

The dying fleas found in the cat cages and by combing are collected, placed in an incubator at 28° C. and 70% relative humidity and after 24 hours are tested for survival/mortality. If the majority of dying fleas die, the test compound is regarded as a flea adulticide, and if the majority survive, the test compound shows "knock-down" activity.

In this test, the compounds of formula I effect at least 80% mortality of the fleas.

10. In vivo Efficacy on Adult *Ctenocephalides felis* on Domestic Cats After Spot-on Treatment The test substances are given to domestic cats as spot-on treatment, the dose varying between 0.5 and 10 mg/kg. On days 1, 3, 7 and 10 after treatment, each cat is exposed to 100 fleas (ca. 50 male and ca. 50 female), depending on the result of previous flea colonisation.

The efficacy (in % reduction in flea numbers) is based on the number of living fleas found after combing for 10 minutes one day after each new flea colonisation, whereby the efficacy in % corresponds to the arithmetic average of the number of living fleas on control animals minus the number of living fleas on the treated animals, divided by the arithmetic average of the number of living fleas on control animals and multiplied by 100.

The dying fleas found in the cat cages and by combing are collected, placed in an incubator at 28° C. and 70% relative humidity and after 24 hours are tested for survival/mortality. If the majority of dying fleas die, the test compound is regarded as a flea adulticide, and if the majority survive, the test compound shows "knock-down" activity.

In this test, the compounds of formula I effect more than 90% mortality of the fleas after 35 days.

11. In vitro Efficacy on Nymphs of *Amblyomma hebraeum*

About 5 fasting nymphs are placed in a polystyrene test tube containing 2 ml of the test compound in solution, suspension or emulsion.

After immersion for 10 minutes, and shaking for 2×10 seconds on a vortex mixer, the test tubes are blocked up with a tight wad of cotton wool and rotated. As soon as all the liquid has been soaked up by the cotton wool ball, it is pushed half-way into the test tube which is still being rotated, so that most of the liquid is squeezed out of the cotton-wool ball and flows into a Petri dish below.

The test tubes are then kept at room temperature in a room with daylight until evaluated. After 14 days, the test tubes are immersed in a beaker of boiling water. If the ticks begin to move in reaction to the heat, the test substance is inactive at the tested concentration, otherwise the ticks are regarded as dead and the test substances regarded as active at the tested concentration. All substances are tested in a concentration range of 0.1 to 100 ppm.

In this test, the compounds of formula I effect more than 80% mortality of the ticks.

12. Activity Against *Dermanyssus gallinae*

2 to 3 ml of a solution containing 10 ppm active ingredient, and ca. 200 mites (*Dermanyssus gallinae*) at different stages of development are added to a glass container which is open at the top. Then the container is closed with a wad of cotton wool, shaken for 10 minutes until the mites are completely wet, and then inverted briefly so that the remaining test solution can be absorbed by the cotton wool. After 3 days, the mortality of the mites is determined by counting the dead individuals and indicated as a percentage.

The compounds of formula I show good activity against *Dermanyssus gallinae*.

13. Activity Against *Musca domestica*

A sugar cube is treated with a solution of the test substance in such a way that the concentration of test substance in the sugar, after drying over night, is 250 ppm. The cube treated in this way is placed on an aluminium dish with wet cotton wool and 1.0 adult *Musca domestica* of an OP-resistant strain, covered with a beaker and incubated at 25° C. The mortality rate is determined after 24 hours.

In this test, the compounds of formula I show good activity against *Musca domestica*.

What we claim is:

1. A compound of formula

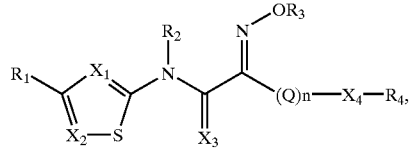    I wherein $R_1$ is hydrogen, halogen, $C_1$–$C_6$-alkyl, $C_1$–$C_6$-alkoxy, $C_1$–$C_6$-haloalkyl or unsubstituted or mono- to penta-substituted phenyl, wherein the substituents are selected from the group consisting of $C_1$–$C_6$-alkyl, $C_1$–$C_6$-haloalkyl, $C_1$–$C_6$-alkoxy, aryloxy, halogen, cyano and nitro, wherein the substituents may be identical or different;

$R_2$ is hydrogen, $C_1$–$C_6$-alkyl, ($C_1$–$C_6$-alkylene)phenyl, pyridyl, $COOR_6$, $CONR_7R_8$, $CORE$, allyl or $CH_2$—$O$—$R_6$;

$R_3$ is $C_1$–$C_6$-alkyl;

$R_4$ is unsubstituted or substituted phenyl, unsubstituted or substituted benzyl or unsubstituted or substituted heterocyclyl, whereby each of the substituents, independently of each other, is selected from the group consisting of $C_1$–$C_6$-alkyl, $C_1$–$C_6$-haloalkyl, $C_1$–$C_6$-alkoxy, aryloxy, halogen, cyano, hydroxy, amino and nitro, wherein the substituents may be identical or different;

$R_6$ is $C_1$–$C_6$-alkyl, phenyl or benzyl;

$R_7$ and $R_8$ independently of one another, are hydrogen or $C_1$–$C_6$-alkyl;

Q is $C_1$–$C_6$-alkylene;

$X_1$ is N or C(CN);

$X_2$ is N, C(CN), C($COOR_6$), C($COR_6$), C($SOR_6$), C($CONR_7R_8$) or C($NO_2$);

$X_3$ and $X_4$, independently of each other, are O or S; and n is 0 or 1.

2. A process for preparing a compound of formula I according to claim 1, comprising reacting a compound of formula

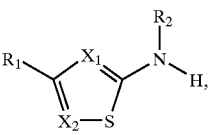    II wherein $R_1$, $R_2$, $X_1$ and $X_2$ are defined as given for formula I with a) a compound of formula

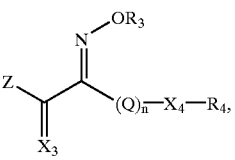    III wherein $X_3$, $X_4$, $R_3$, $R_4$, n and Q are defined as for formula I and Z is a leaving group, or b) a compound of formula

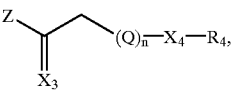    IV wherein $X_4$, $R_4$, n and Q are defined as for formula I, and Z is a leaving group and $X_3$ is O; introducing a nitroso group into the resulting product, producing an oxime; and reacting the oxime with a compound of formula

    V, wherein $X_3$ is defined as for formula I and $X_5$ is a leaving group.

3. A composition for controlling pests, which contains at least one compound of formula I according to claim 1 as an active ingredient, in addition to carriers and/or dispersants.

4. A method of controlling pests, wherein a pesticidally active amount of at least one compound of formula I according to claim 1 is used on the pests or on a locus thereof.

5. A method for controlling pests according to claim 4, wherein the pests are parasites on a warm-blooded animal.

6. A method for preparing a pharmaceutical composition against parasites, comprising preparing a compound of formula I of claim 1.

* * * * *